US011312071B2

United States Patent
Asgeirsson et al.

(10) Patent No.: US 11,312,071 B2
(45) Date of Patent: Apr. 26, 2022

(54) ADDITIVE MANUFACTURING SYSTEM, METHOD AND CORRESPONDING COMPONENTS FOR MAKING ELASTOMERIC STRUCTURES

(71) Applicant: Ossur Iceland ehf, Reykjavik (IS)

(72) Inventors: Sigurdur Asgeirsson, Foothill Ranch, CA (US); Jiri Dlab, Foothill Ranch, CA (US); Larus Sigfusson, Foothill Ranch, CA (US)

(73) Assignee: OSSUR ICELAND EHF, Reykjavik (IS)

( * ) Notice: Subject to any disclaimer, the term of this patent is extended or adjusted under 35 U.S.C. 154(b) by 276 days.

(21) Appl. No.: 16/681,096

(22) Filed: Nov. 12, 2019

(65) Prior Publication Data
US 2020/0147875 A1 May 14, 2020

Related U.S. Application Data

(60) Provisional application No. 62/759,237, filed on Nov. 12, 2018, provisional application No. 62/760,030, filed on Nov. 12, 2018.

(51) Int. Cl.
*B29C 64/209* (2017.01)
*B29C 64/118* (2017.01)
(Continued)

(52) U.S. Cl.
CPC ........ *B29C 64/209* (2017.08); *A61F 2/30907* (2013.01); *A61F 2/7812* (2013.01);
(Continued)

(58) Field of Classification Search
CPC .... B29C 64/118; B29C 64/209; C12M 23/28; C12M 33/00; C12M 37/00; C12M 41/18; C12M 41/48
See application file for complete search history.

(56) References Cited

U.S. PATENT DOCUMENTS 529,719 A 11/1894 Eils
541,275 A 6/1895 Hepp
(Continued)

FOREIGN PATENT DOCUMENTS

AT 6615 U1 1/2004
CA 2398059 A1 8/2001
(Continued)

OTHER PUBLICATIONS

"MED-6345; Soft Silicone Adhesive," NuSil, Nov. 2018, retrieved from https://nusil.com/en/product/MED-6345_soft-silicone-adhesive?h=MED-6345 on Dec. 15, 2021 3 Pages. (Year: 2019).*
(Continued)

*Primary Examiner* — Joseph S Del Sole
*Assistant Examiner* — Manley L Cummins, IV
(74) *Attorney, Agent, or Firm* — Workman Nydegger

(57) ABSTRACT

A system for additive manufacturing a medical device, the system comprising a first dispensing system, a second dispensing system, a deposition apparatus, and a deposition substrate on a surface of which the deposition apparatus is configured to deposit at least one elastomeric material into a filament. The deposition apparatus receives the at least one elastomeric material from the first and second dispensing systems in proportions effecting a desired property in the medical device. The deposition apparatus may comprise heating and/or cooling elements, a sonic vibration module, and/or a pneumatic suck-back valve. The deposition substrate may have a configuration corresponding to a desired shape of the medical device and is configured to rotate and/or translate relative to the deposition apparatus. The system comprises a controller configured to control the deposition.

14 Claims, 13 Drawing Sheets

(51) Int. Cl.
*B29C 64/245* (2017.01)
*B29C 64/255* (2017.01)
*B29C 64/295* (2017.01)
*B29C 64/343* (2017.01)
*B29C 64/227* (2017.01)
*A61F 2/30* (2006.01)
*A61F 2/78* (2006.01)
*A61F 2/80* (2006.01)
*B33Y 30/00* (2015.01)
*B33Y 40/00* (2020.01)

(52) U.S. Cl.
CPC .............. *A61F 2/80* (2013.01); *B29C 64/118* (2017.08); *B29C 64/227* (2017.08); *B29C 64/245* (2017.08); *B29C 64/255* (2017.08); *B29C 64/295* (2017.08); *B29C 64/343* (2017.08); *A61F 2002/30919* (2013.01); *A61F 2002/7818* (2013.01); *A61F 2002/7837* (2013.01); *A61F 2250/0076* (2013.01); *B33Y 30/00* (2014.12); *B33Y 40/00* (2014.12)

(56) References Cited

U.S. PATENT DOCUMENTS

| | | |
|---|---|---|
| 2,104,742 A | 1/1938 | Fleischer |
| 2,414,716 A | 1/1947 | Carson |
| 2,490,586 A | 12/1949 | Embree |
| 2,680,501 A | 6/1954 | Cunningham |
| 2,765,159 A | 10/1956 | Garofalo |
| 3,019,552 A | 2/1962 | Schleich |
| 3,081,514 A | 3/1963 | Griswold |
| 3,125,195 A | 3/1964 | Moore |
| 3,389,451 A | 6/1968 | Speca et al. |
| 3,391,048 A | 7/1968 | Dyer et al. |
| 3,468,748 A | 9/1969 | Bassett |
| 3,661,670 A | 5/1972 | Pierpont, Jr. |
| 4,107,870 A | 8/1978 | Ausnit |
| 4,205,152 A | 5/1980 | Mizuguchi et al. |
| 4,290,170 A | 9/1981 | Brookstein et al. |
| 4,323,756 A * | 4/1982 | Brown .................. C22C 19/056 219/121.66 |
| 4,575,330 A | 3/1986 | Hull |
| 4,674,580 A | 6/1987 | Schuh et al. |
| 4,735,418 A | 4/1988 | Engel |
| 4,777,859 A | 10/1988 | Plummer, Jr. |
| 4,867,834 A | 9/1989 | Alenskis et al. |
| 4,978,564 A | 12/1990 | Douglas |
| 5,045,147 A | 9/1991 | Benson et al. |
| 5,156,629 A | 10/1992 | Shane et al. |
| 5,281,181 A | 1/1994 | McCollum |
| 5,288,287 A | 2/1994 | Castillo et al. |
| 5,372,283 A | 12/1994 | Schmitkons et al. |
| 5,387,245 A | 2/1995 | Fay et al. |
| 5,571,208 A | 11/1996 | Caspers |
| 5,594,652 A | 1/1997 | Penn et al. |
| 5,603,122 A | 2/1997 | Kania |
| 5,702,489 A | 12/1997 | Slemker |
| 5,713,837 A * | 2/1998 | Grim ................... A61F 5/0111 602/21 |
| 5,781,652 A | 7/1998 | Pratt |
| 5,853,313 A | 12/1998 | Zheng |
| 5,888,216 A | 3/1999 | Haberman |
| 5,901,060 A | 5/1999 | Schall et al. |
| 5,928,803 A | 7/1999 | Yasuda |
| 6,012,494 A | 1/2000 | Balazs |
| 6,024,712 A | 2/2000 | Iglesias et al. |
| 6,136,039 A | 10/2000 | Kristinsson et al. |
| 6,165,406 A | 12/2000 | Jang et al. |
| 6,176,875 B1 | 1/2001 | Lenker et al. |
| 6,231,616 B1 | 5/2001 | Helmy |
| 6,231,617 B1 | 5/2001 | Fay |
| 6,264,199 B1 | 7/2001 | Schaedel |
| 6,305,769 B1 | 10/2001 | Thayer et al. |
| 6,358,453 B1 | 3/2002 | Slemker et al. |
| 6,454,972 B1 * | 9/2002 | Morisette .............. B29C 64/118 264/39 |
| 6,463,351 B1 | 10/2002 | Clynch |
| 6,508,842 B1 | 1/2003 | Caspers |
| 6,554,868 B1 | 4/2003 | Caspers |
| 6,592,539 B1 | 7/2003 | Einarsson et al. |
| 6,626,952 B2 | 9/2003 | Janusson et al. |
| 6,630,093 B1 | 10/2003 | Jones |
| 6,645,253 B2 | 11/2003 | Caspers |
| 6,926,742 B2 | 8/2005 | Caspers et al. |
| 6,968,246 B2 | 11/2005 | Watson et al. |
| 6,991,444 B1 | 1/2006 | Laghi |
| 7,007,370 B2 | 3/2006 | Gracias et al. |
| 7,118,602 B2 | 10/2006 | Bjarnason |
| 7,160,612 B2 | 1/2007 | Magill et al. |
| 7,162,322 B2 | 1/2007 | Arbogast et al. |
| 7,169,189 B2 | 1/2007 | Bjarnason et al. |
| 7,216,678 B2 | 5/2007 | Baer |
| 7,225,045 B2 | 5/2007 | Gothait et al. |
| 7,225,050 B2 | 5/2007 | Sutula, Jr. |
| 7,300,619 B2 | 11/2007 | Napadensky et al. |
| 7,351,264 B2 | 4/2008 | Wilson |
| 7,438,843 B2 | 10/2008 | Asgeirsson |
| 7,447,558 B2 | 11/2008 | Pratt |
| 7,500,846 B2 | 3/2009 | Eshed et al. |
| 7,575,807 B1 | 8/2009 | Barvosa-Carter et al. |
| 7,708,709 B2 | 5/2010 | Brewer |
| 7,785,331 B2 | 8/2010 | Leisinger et al. |
| 7,851,122 B2 | 12/2010 | Napadensky |
| 7,862,624 B2 | 1/2011 | Tran |
| 7,867,286 B2 | 1/2011 | Einarsson |
| 8,082,696 B2 | 12/2011 | Oliver et al. |
| 8,142,860 B2 | 3/2012 | Vanmaele et al. |
| 8,246,888 B2 | 8/2012 | Hopkins et al. |
| 8,308,817 B2 | 11/2012 | Egilsson et al. |
| 8,366,789 B2 | 2/2013 | Summit |
| 8,424,249 B2 | 4/2013 | Oliver |
| 8,475,074 B1 | 7/2013 | Henry |
| 8,523,951 B2 | 9/2013 | Kania |
| 8,652,602 B1 | 2/2014 | Dolla |
| 8,668,744 B2 | 3/2014 | McCarthy |
| 8,795,386 B2 | 8/2014 | Pianykh et al. |
| 8,906,113 B2 | 12/2014 | Mosler et al. |
| 8,940,057 B2 | 1/2015 | Asgeirsson |
| 8,992,183 B2 | 3/2015 | Perich et al. |
| 9,002,496 B2 | 4/2015 | Elsey |
| 9,079,337 B2 | 7/2015 | Lipton et al. |
| D744,719 S | 12/2015 | Amarasiriwardena |
| 9,364,348 B2 | 6/2016 | Sandahl |
| 9,398,963 B2 | 7/2016 | King |
| 9,486,333 B2 | 11/2016 | Wang et al. |
| 9,550,327 B2 | 1/2017 | Swanson et al. |
| 9,669,586 B2 | 6/2017 | Page |
| 9,757,256 B2 | 9/2017 | Sandahl |
| 9,814,607 B2 | 11/2017 | Zhe et al. |
| 9,901,451 B2 | 2/2018 | Conway et al. |
| 9,970,140 B2 | 5/2018 | Taninaka et al. |
| 9,993,357 B2 | 6/2018 | Jonsson |
| 9,993,973 B1 | 6/2018 | Barnhart |
| 10,005,235 B2 | 6/2018 | Millar |
| 10,022,917 B2 | 7/2018 | Pax |
| 10,028,845 B2 | 7/2018 | Jonasson et al. |
| 10,064,726 B1 | 9/2018 | Wei |
| 10,076,880 B2 | 9/2018 | Page |
| 10,166,726 B2 | 1/2019 | Fripp et al. |
| 10,286,601 B2 | 5/2019 | Chang |
| 10,513,089 B2 | 12/2019 | Tibbits et al. |
| 10,543,643 B2 | 1/2020 | Sachs et al. |
| 10,549,505 B2 | 2/2020 | Tibbits et al. |
| 10,633,772 B2 | 4/2020 | Tibbits et al. |
| 2002/0043950 A1 | 4/2002 | Yim et al. |
| 2002/0104973 A1 | 8/2002 | Kerekes |
| 2002/0116847 A1 | 8/2002 | Yen |
| 2002/0125790 A1 | 9/2002 | Horning et al. |
| 2003/0090034 A1 | 5/2003 | Mülhaupt et al. |
| 2003/0177749 A1 | 9/2003 | Jen |
| 2003/0181990 A1 | 9/2003 | Phillips |
| 2004/0030411 A1 | 2/2004 | Caspers |

(56) References Cited

U.S. PATENT DOCUMENTS

| | | | |
|---|---|---|---|
| 2004/0098136 A1 | 5/2004 | Caspers | |
| 2004/0137178 A1 | 7/2004 | Janusson et al. | |
| 2004/0143345 A1 | 7/2004 | Caspers | |
| 2004/0197519 A1 | 10/2004 | Elzey et al. | |
| 2004/0243251 A1* | 12/2004 | Carstens | A61F 2/80 623/34 |
| 2004/0244309 A1 | 12/2004 | Raue | |
| 2004/0260402 A1 | 12/2004 | Baldini et al. | |
| 2005/0101693 A1 | 5/2005 | Arbogast et al. | |
| 2005/0119777 A1 | 6/2005 | Arbogast et al. | |
| 2005/0149202 A1 | 7/2005 | Schaffer et al. | |
| 2005/0165338 A1* | 7/2005 | Iglesias | A61F 5/0118 602/21 |
| 2005/0227560 A1 | 10/2005 | Allred, III | |
| 2005/0265569 A1* | 12/2005 | Langberg | H04R 5/02 381/334 |
| 2006/0016507 A1 | 1/2006 | Baer | |
| 2006/0020348 A1 | 1/2006 | Slemker et al. | |
| 2006/0159869 A1 | 7/2006 | Kramer et al. | |
| 2006/0184231 A1 | 8/2006 | Rucker | |
| 2006/0282175 A1* | 12/2006 | Haines | A61F 2/70 623/24 |
| 2007/0036964 A1 | 2/2007 | Rosenberger et al. | |
| 2007/0055383 A1 | 3/2007 | King | |
| 2007/0073410 A1 | 3/2007 | Raugel | |
| 2007/0106173 A1 | 5/2007 | Korotko et al. | |
| 2007/0134486 A1 | 6/2007 | Bansal et al. | |
| 2007/0150069 A1 | 6/2007 | Takami et al. | |
| 2007/0162154 A1 | 7/2007 | Scott | |
| 2007/0163305 A1 | 7/2007 | Baer et al. | |
| 2007/0191965 A1 | 8/2007 | Colvin et al. | |
| 2007/0276510 A1* | 11/2007 | Becker | B29C 70/30 623/33 |
| 2008/0027199 A1 | 1/2008 | Mazurek et al. | |
| 2008/0039757 A1 | 2/2008 | Nordt, III et al. | |
| 2008/0057809 A1 | 3/2008 | Rock | |
| 2008/0066393 A1 | 3/2008 | Sorenson | |
| 2008/0075850 A1 | 3/2008 | Rock | |
| 2008/0075930 A1 | 3/2008 | Kornbluh et al. | |
| 2008/0105324 A1 | 5/2008 | Baer | |
| 2008/0109103 A1 | 5/2008 | Gershenfeld et al. | |
| 2008/0188949 A1 | 8/2008 | MacKenzie | |
| 2008/0234458 A1 | 9/2008 | West | |
| 2008/0269420 A1 | 10/2008 | Tong et al. | |
| 2009/0176054 A1 | 7/2009 | Laib et al. | |
| 2009/0218307 A1 | 9/2009 | Davies et al. | |
| 2009/0233067 A1 | 9/2009 | Doornheim et al. | |
| 2009/0240344 A1 | 9/2009 | Colvin et al. | |
| 2009/0248168 A1 | 10/2009 | Tuke et al. | |
| 2010/0023149 A1 | 1/2010 | Sanders et al. | |
| 2010/0161076 A1 | 6/2010 | Pallari | |
| 2010/0168439 A1 | 7/2010 | Olson | |
| 2010/0191360 A1 | 7/2010 | Napadensky et al. | |
| 2011/0270414 A1 | 11/2011 | Laghi et al. | |
| 2011/0285052 A1 | 11/2011 | Wigand et al. | |
| 2012/0037263 A1 | 2/2012 | Malloy | |
| 2012/0068378 A1 | 3/2012 | Swanson et al. | |
| 2012/0091744 A1 | 4/2012 | McKnight et al. | |
| 2012/0094060 A1 | 4/2012 | Gershenfeld et al. | |
| 2012/0109336 A1 | 5/2012 | Laghi et al. | |
| 2012/0133080 A1 | 5/2012 | Moussa et al. | |
| 2012/0137611 A1 | 6/2012 | Oliver | |
| 2012/0241993 A1 | 9/2012 | Lipton et al. | |
| 2012/0308805 A1 | 12/2012 | Sella | |
| 2013/0001834 A1 | 1/2013 | El-Shiblani et al. | |
| 2013/0040091 A1 | 2/2013 | Dikovsky et al. | |
| 2013/0046394 A1 | 2/2013 | Lipschutz et al. | |
| 2013/0073068 A1 | 3/2013 | Napadensky | |
| 2013/0078415 A1 | 3/2013 | Rock | |
| 2013/0089642 A1 | 4/2013 | Lipson et al. | |
| 2013/0103125 A1* | 4/2013 | Radspieler | A61F 7/02 607/104 |
| 2013/0150982 A1* | 6/2013 | Mosler | A61F 2/80 623/34 |
| 2013/0246018 A1 | 9/2013 | Spadaccini et al. | |
| 2013/0249981 A1 | 9/2013 | Nakagawa et al. | |
| 2013/0282141 A1* | 10/2013 | Herr | A61F 2/80 623/33 |
| 2014/0013962 A1 | 1/2014 | Lipton et al. | |
| 2014/0037873 A1 | 2/2014 | Cheung et al. | |
| 2014/0050811 A1 | 2/2014 | Lipton et al. | |
| 2014/0059734 A1 | 3/2014 | Toronjo | |
| 2014/0101816 A1 | 4/2014 | Toronjo | |
| 2014/0163445 A1 | 6/2014 | Pallari et al. | |
| 2014/0188260 A1 | 7/2014 | Layman et al. | |
| 2014/0276300 A1* | 9/2014 | Reinhardt | A61F 5/0104 602/5 |
| 2014/0277585 A1 | 9/2014 | Kelley et al. | |
| 2014/0311187 A1 | 10/2014 | Amarasiriwardena et al. | |
| 2015/0010461 A1* | 1/2015 | Cronin | C07D 471/04 423/463 |
| 2015/0014881 A1 | 1/2015 | Elsey | |
| 2015/0017411 A1 | 1/2015 | Wilkie et al. | |
| 2015/0032227 A1* | 1/2015 | Kettwig | A61F 2/80 623/33 |
| 2015/0075033 A1 | 3/2015 | Cross et al. | |
| 2015/0142150 A1 | 5/2015 | Layman et al. | |
| 2015/0142159 A1* | 5/2015 | Chang | B29C 64/106 700/119 |
| 2015/0158244 A1* | 6/2015 | Tibbits | B29C 71/0009 428/516 |
| 2015/0174885 A1 | 6/2015 | Khan | |
| 2015/0250624 A1 | 9/2015 | Mosler et al. | |
| 2015/0297369 A1* | 10/2015 | Mosler | A61F 2/7812 623/36 |
| 2015/0321419 A1 | 11/2015 | Linthicum et al. | |
| 2015/0321420 A1 | 11/2015 | Karpas et al. | |
| 2015/0359644 A1* | 12/2015 | Sanders | A61F 2/80 623/34 |
| 2015/0367375 A1 | 12/2015 | Page | |
| 2016/0000583 A1* | 1/2016 | Ballas | A61F 2/7812 623/26 |
| 2016/0009029 A1 | 1/2016 | Cohen et al. | |
| 2016/0058519 A1* | 3/2016 | Herr | A61F 2/7812 600/438 |
| 2016/0096323 A1 | 4/2016 | Fry et al. | |
| 2016/0101594 A1* | 4/2016 | Tibbits | B32B 5/18 428/64.1 |
| 2016/0167312 A1* | 6/2016 | Feinberg | A61L 27/24 264/239 |
| 2016/0228255 A1 | 8/2016 | Samuelson et al. | |
| 2016/0263827 A1* | 9/2016 | Fripp | B29C 64/124 |
| 2016/0297104 A1 | 10/2016 | Guillemette et al. | |
| 2016/0318247 A1* | 11/2016 | Schlachter | B29C 64/245 |
| 2016/0324666 A1 | 11/2016 | Barberio | |
| 2016/0332382 A1 | 11/2016 | Coward et al. | |
| 2017/0027719 A1* | 2/2017 | Bache | D04B 1/18 |
| 2017/0036402 A1 | 2/2017 | Zachariasen et al. | |
| 2017/0057167 A1* | 3/2017 | van Tooren | B29C 64/245 |
| 2017/0081573 A1 | 3/2017 | Kipke et al. | |
| 2017/0105853 A1 | 4/2017 | Jonsson et al. | |
| 2017/0106594 A1* | 4/2017 | Gardiner | B29C 64/135 |
| 2017/0120535 A1* | 5/2017 | MacCurdy | B29C 64/40 |
| 2017/0173879 A1 | 6/2017 | Myerberg et al. | |
| 2017/0190121 A1 | 7/2017 | Aggarwal et al. | |
| 2017/0203509 A1 | 7/2017 | Stieghorst et al. | |
| 2017/0210064 A1 | 7/2017 | Aw et al. | |
| 2017/0216056 A1 | 8/2017 | Hill et al. | |
| 2017/0239888 A1 | 8/2017 | Ruiz et al. | |
| 2017/0259502 A1 | 9/2017 | Chapiro et al. | |
| 2017/0312981 A1 | 11/2017 | Selbertinger et al. | |
| 2017/0335268 A1* | 11/2017 | Maggiore | B29C 48/02 |
| 2018/0021140 A1 | 1/2018 | Angelini et al. | |
| 2018/0036952 A1 | 2/2018 | Hocker et al. | |
| 2018/0056602 A1 | 3/2018 | Susnjara et al. | |
| 2018/0098919 A1 | 4/2018 | Pallari et al. | |
| 2018/0112167 A1* | 4/2018 | Kang | C12N 5/0062 |
| 2018/0153716 A1 | 6/2018 | Martin | |
| 2018/0204379 A1* | 7/2018 | Mendoza | G06K 9/00214 |
| 2018/0235779 A1 | 8/2018 | Dudding | |
| 2018/0236723 A1 | 8/2018 | Susnjara et al. | |
| 2018/0281295 A1 | 10/2018 | Tibbits et al. | |

(56) References Cited

U.S. PATENT DOCUMENTS

| | | | |
|---|---|---|---|
| 2018/0281340 A1 | 10/2018 | Brienza et al. | |
| 2018/0296343 A1 | 10/2018 | Wei | |
| 2018/0353308 A1 | 12/2018 | Tompkins | |
| 2018/0368996 A1 | 12/2018 | Van Vliet et al. | |
| 2018/0369451 A1* | 12/2018 | Rapoport | C09D 11/03 |
| 2018/0370141 A1 | 12/2018 | Eller et al. | |
| 2019/0039309 A1 | 2/2019 | Busbee et al. | |
| 2019/0039310 A1 | 2/2019 | Busbee et al. | |
| 2019/0053917 A1* | 2/2019 | Mosler | A61F 2/50 |
| 2019/0053919 A1 | 2/2019 | Egilsson et al. | |
| 2019/0070345 A1 | 3/2019 | McBride et al. | |
| 2019/0099952 A1 | 4/2019 | MacNeish, III et al. | |
| 2019/0106593 A1 | 4/2019 | Kenney et al. | |
| 2019/0142406 A1 | 5/2019 | Amplatz et al. | |
| 2019/0183663 A1 | 6/2019 | Will et al. | |
| 2019/0270240 A1* | 9/2019 | Wolf | C08L 83/04 |
| 2019/0272346 A1* | 9/2019 | Weeger | B29C 61/0608 |
| 2019/0336749 A1* | 11/2019 | Daglow | A61N 1/0534 |
| 2019/0344494 A1* | 11/2019 | Cropper | B33Y 70/00 |
| 2020/0016833 A1 | 1/2020 | Yuwaki et al. | |
| 2020/0100920 A1* | 4/2020 | Finke | A61F 2/5044 |
| 2020/0247053 A1* | 8/2020 | Rodriguez | B29C 64/118 |
| 2020/0289295 A1* | 9/2020 | Koppe | A61F 2/5044 |
| 2020/0324464 A1* | 10/2020 | Reese | B29C 64/00 |
| 2021/0030566 A1* | 2/2021 | Siewert | A61F 5/0102 |
| 2021/0068987 A1* | 3/2021 | Koppe | B33Y 80/00 |
| 2021/0145613 A1 | 5/2021 | Anderson et al. | |
| 2021/0162651 A1* | 6/2021 | Schweizer | B29C 64/209 |
| 2021/0338457 A1* | 11/2021 | Albrecht-Laatsch | G01B 15/04 |

FOREIGN PATENT DOCUMENTS

| | | | |
|---|---|---|---|
| CA | 3114854 | * | 4/2020 |
| CN | 103876263 A | | 6/2014 |
| CN | 106003728 A | | 10/2016 |
| CN | 107351375 A | | 11/2017 |
| CN | 106667629 B | | 4/2018 |
| CN | 109414330 A | | 3/2019 |
| CN | 110461277 A | | 11/2019 |
| DE | 917687 C | | 9/1954 |
| DE | 10018987 A1 | | 10/2001 |
| DE | 10153796 B4 | | 6/2003 |
| DE | 20309318 U1 | | 9/2003 |
| DE | 202008015143 U1 | | 2/2009 |
| DE | 202009000527 U1 | | 3/2009 |
| DE | 102011119591 B3 | | 5/2013 |
| DE | 102012009757 A1 | | 12/2013 |
| DE | 102013102471 A1 | | 9/2014 |
| DE | 102014011373 A1 | | 2/2016 |
| DE | 102014219570 B4 | | 5/2016 |
| DE | 102016201002 A1 | | 7/2017 |
| DE | 102016108631 A1 | | 11/2017 |
| DE | 202017106997 U1 | | 1/2018 |
| DE | 102017106903 B3 | | 7/2018 |
| DE | 202019100501 U1 | | 3/2019 |
| DE | 102012017324 B4 | | 4/2019 |
| DE | 102017126465 A1 | | 5/2019 |
| DE | 102018106573 A1 | | 9/2019 |
| DE | 102018124516 A1 | | 4/2020 |
| DE | 102018127117 A1 | | 4/2020 |
| DE | 102012022484 B4 | | 6/2020 |
| DE | 102018131550 A1 | | 6/2020 |
| DE | 102018133486 A1 | | 6/2020 |
| EP | 1274559 B1 | | 1/2003 |
| EP | 0876130 B1 | | 3/2006 |
| EP | 1854621 B1 | | 11/2007 |
| EP | 2090273 A2 | | 8/2009 |
| EP | 2568935 A2 | | 3/2013 |
| EP | 2599464 A1 | | 6/2013 |
| EP | 3100704 A1 | | 12/2016 |
| EP | 2599464 B1 | | 1/2017 |
| EP | 3156216 A1 | | 4/2017 |
| EP | 3243632 A1 | | 11/2017 |
| EP | 3300700 A3 | | 7/2018 |
| EP | 3454792 A1 | | 3/2019 |
| FR | 1243060 A | | 10/1960 |
| FR | 1331581 A | | 7/1963 |
| FR | 2095097 A5 | | 2/1972 |
| FR | 2479923 A1 | | 10/1981 |
| FR | 2583334 A1 | | 12/1986 |
| FR | 2956590 B1 | | 8/2011 |
| GB | 2455167 A | | 6/2009 |
| JP | H0742024 A | | 2/1995 |
| JP | 2003533367 A | | 11/2003 |
| WO | 0069747 A1 | | 11/2000 |
| WO | 0178968 A1 | | 10/2001 |
| WO | 03016067 A2 | | 2/2003 |
| WO | 03051241 A1 | | 6/2003 |
| WO | 2006113585 A2 | | 10/2006 |
| WO | 2006135851 A2 | | 12/2006 |
| WO | 2013072064 A1 | | 5/2013 |
| WO | 2013121230 A1 | | 8/2013 |
| WO | 2013142343 A1 | | 9/2013 |
| WO | 2014025089 A1 | | 2/2014 |
| WO | 2014130878 A1 | | 8/2014 |
| WO | 2014144985 A1 | | 9/2014 |
| WO | 2015017421 A2 | | 2/2015 |
| WO | 2015059502 A1 | | 4/2015 |
| WO | 2015084422 A1 | | 6/2015 |
| WO | 2015139095 A1 | | 9/2015 |
| WO | 2015197495 A1 | | 12/2015 |
| WO | 2016033469 A1 | | 3/2016 |
| WO | 2016057853 A1 | | 4/2016 |
| WO | 2017011753 A1 | | 1/2017 |
| WO | 2017012888 A1 | | 1/2017 |
| WO | 2017019681 A1 | | 2/2017 |
| WO | 2017062690 A1 | | 4/2017 |
| WO | 2017079475 A1 | | 5/2017 |
| WO | 2017081040 A1 | | 5/2017 |
| WO | 2017136405 A1 | | 8/2017 |
| WO | 2017194479 A1 | | 11/2017 |
| WO | 2018044759 A1 | | 3/2018 |
| WO | 2018054966 A1 | | 3/2018 |
| WO | 2018088965 A1 | | 5/2018 |
| WO | 2018151923 A1 | | 8/2018 |
| WO | 2018183803 A1 | | 10/2018 |
| WO | 2018187514 A1 | | 10/2018 |
| WO | 2019091716 A1 | | 5/2019 |
| WO | 2019110170 A1 | | 6/2019 |
| WO | 2019179894 A1 | | 9/2019 |
| WO | 2019219514 A1 | | 11/2019 |
| WO | 2020069817 A1 | | 4/2020 |
| WO | 2020074374 A1 | | 4/2020 |
| WO | 2020120187 A1 | | 6/2020 |
| WO | 2020126501 A1 | | 6/2020 |
| WO | 2021101806 A1 | | 5/2021 |

OTHER PUBLICATIONS

"MED-4901; Liquid Silicone Rubber," NuSil, Nov. 2018, retrieved from https://nusil.com/product/med-4901_liquid-silicone-rubber on Nov. 11, 2019, 3 Pages.

"MED-6345; Soft Silicone Adhesive," NuSil, Nov. 2018, retrieved from https://nusil.com/en/product/MED-6345_soft-silicone-adhesive?h=MED-6345 on Nov. 11, 2019, 3 Pages.

International Search Report from PCT Application No. PCT/US2019/060863, dated Apr. 15, 2020.

International Search Report from PCT Application No. PCT/US2019/060881, dated Apr. 20, 2020.

Hsu, L.H.: "The development of a rapid prototyping prosthetic socket coated with a resin layer for transtibial amputees", Prosthetics and Orthotics International, vol. 34, No. 1, Mar. 1, 2010 (Mar. 1, 2010), pp. 37-45.

Nicholas Herbert et al, "A preliminary investigation into the development of 3-D printing of prosthetic sockets", Journal of Rehabilitation Research and Development, vol. 42, No. 2, Jan. 1, 2005 (Jan. 1, 2005), US, pp. 141.

Klute et al., "Prosthetic Liners for Lower Limb Amputees: A Review of the Literature," Prosthetics and Orthotics International, vol. 34, No. 2, Jun. 2010, pp. 146-153.

Franzino, "3 Ways to Adhere Silicone to Silicone," Albright Technologies Monthly Insider, Issue 17, Mar. 2013, 2 Pages.

(56) References Cited

OTHER PUBLICATIONS

"CF19-2186; Medium Cure Rate, General Purpose Silicone Elastomer," NuSil, May 21, 2014, retrieved from https://nusil.com/en/product/CF19-2186_medium-cure-rate-general-purpose-silicone-elastomer?h=cf19 on Jan. 3, 2020.
"MED-4950; Liquid Silicone Rubber," NuSil, May 16, 2014, retrieved from https://nusil.com/en/product/MED-4950_liquid-silicone-rubber?h=med-4950 on Jan. 3, 2020, 3 Pages.
Ventola, "Medical Applications for 3D Printing: Current and Projected Uses," P&T, vol. 39, No. 10, Oct. 2014, pp. 704-712.
Femmer et al., "Print Your Own Membrane: Direct Rapid Prototyping of Polydimethylsiloxane," Royal Society of Chemistry, vol. 14, 2014, pp. 2610-2613.
"A True Rotary 3D Printer?" element14, Jun. 27, 2015, retrieved from www.element14.com/community/thread/25031a-true-rotary-3, Oct. 22, 2018.
Ostermeier, "3D Printing With Silicone," Assembly Magazine, Oct. 2, 2015, pp. 1-4.
Coulter et al., "4D Printing Inflatable Silicone Structures," 3D Printing and Additive Manufacturing, vol. 2, No. 3, 2015, pp. 1-6.
Cagle, "A Computational Tool to Enhance Clinical Selection of Prosthetic Liners for People with Lower Limb Amputation," University of Washington, 2016, pp. 1-154.
Hoy, "Design and Implementation of a Three-Dimensional Printer Using a Cylindrical Printing Process," Electrical Engineering Department, California Polytechnic State University, 2016, pp. 1-31.
Momeni et al., "A Review of 4D Printing," Materials and Design, vol. 122, Mar. 1, 2017, pp. 42-79.
O'Bryan et al., "Self-Assembled Micro-Organogels for 3D Printing Silicone Structures," Science Advances, vol. 3, May 10, 2017, pp. 1-8.
Rios, "Evaluation of Advanced Polymers for Additive Manufacturing," Oak Ridge National Laboratory, Sep. 8, 2017, pp. 1-22.
"Rethinking Foam-Carbon's Lattice Innovation," retrieved from www.carbon3d.com, Dec. 6, 2017, pp. 1-9.
Kiessling et al., "Gravity-Drawn Silicone Filaments: Production, Characterization, and Wormlike Chain Dynamics," American Chemical Society, Applied Materials & Interfaces, vol. 9, 2017, pp. 39916-39920.
Low et al., "Perspective on 3D Printing of Separation Membranes and Comparison to Related Unconventional Fabrication Techniques," Journal of Membrane Science, 2017, pp. 596-613.
Tian et al., "Silicone Foam Additive Manufacturing by Liquid Rope Coiling," Science Direct, 2017, pp. 196-201.
Dhokia et al., "The Design and Manufacture of a Prototype Personalized Liner for Lower Limb Amputees," Science Direct, 2017, pp. 476-481.
Jasiuk et al., "An Overview on Additive Manufacturing of Polymers," The Minerals, Metal & Materials Society, vol. 70, No. 3, Jan. 25, 2018, pp. 275-283.
Woodford, "Centrifuges," Jun. 24, 2018, retrieved from www.explainthatstuff.com/centrifuges on Nov. 7, 2018, pp. 1-10.
"How Liners Work," Ottobock, retrieved from www.ottobockus.com/prosthetics on Oct. 22, 2018, 1 Page.
"Technology: The Process in a Nutshell," Spectroplast AG, retrieved from www.spectroplast.com/technology on Oct. 31, 2018, pp. 1-5.
Liravi et al., "A Hybrid Additive Manufacturing Method for the Fabrication of Silicone Bio-Structures: 3D Printing Optimization and Surface Characterization," Elsevier: Materials and Design, 2018, pp. 46-61.
Ruiz et al., "3D Printing Assisted Method of Manufacturing a Perforated Silicone Prosthetic Limb Liner," RESNA Annual Conference, 2017, pp. 1-4.
Zhakeyev et al., "Additive Manufacturing: Unlocking the Evolution of Energy Materials," Advanced Science, vol. 4 2017, pp. 1-44.
Javaid et al., "Current Status and Challenges of Additive Manufacturing in Orthopaedics: An Overview," Journal of Clinical Orthopaedics and Trauma, 2019. pp. 380-386.
Mccoll et al., "Design and Fabrication of Melt Electrowritten Tubes Using Intuitive Software," Materials and Design , 2018, pp. 46-58.
"3D Printing of Silicone Parts in Additive Manufacturing," Capri Systec Ltd, May 22, 2018, pp. 1-3.
Li et al., "Review of 3D Printable Hydrogels and Constructs," Materials and Design, Issue 159, 2018, pp. 20-38.
Helmenstine, "What Is Centripetal Force? Definition and Equations," Thought Co., Sep. 21, 2018, pp. 1-3.
Liravi et al., "Additive Manufacturing of Silicone Structures: A Review and Prospective," Additive Manufacturing, Issue 24, 2018, pp. 232-242.
"3D Printing With Silicones—A Breakthrough in Additive Manufacturing," retrieved from www.plastics.gl/3d-printing-2/3d-printing-with-silicones-a-breakthrough-in-additive-manufacturing/ on Oct. 31, 2018.
Culmone et al., "Additive Manufacturing of Medical Instruments: A State-of-the-Art Review," Additive Manufacturing, Issue 27, 2019, pp. 461-473.
Ooi, "How to 3D Print Rubber-Like Materials," All3DP, retrieved from https://all3dp.com/2/how-to-3d-print-rubber-like-materials/ on Aug. 13, 2019, pp. 1-7.
"Progressive Cavity Pumps—Volumetric Dosing Systems," retrieved from www.viscotec.de/en/technology/ retrieved on Aug. 13, 2019.
Yuan et al., "Polymeric Composites for Powder-Based Additive Manufacturing: Materials and Applications," Progress in Polymer Science, vol. 91, 2019, pp. 141-168.
Chen et al., "3D Printed Multifunctional, Hyperelastic Silicone Rubber Foam," Advanced Functional Materials, vol. 29, Issue 1900469, 2019, pp. 1-9.
"About the Silicone Molding Design Manual," Albright Technologies 6th Edition, pp. 1-248.
Porter et al., "Additive Manufacturing Utilizing Stock Ultraviolet Curable Silicone," Solid Freeform Fabrication 2017: Proceedings of the 28th Annual International Solid Freeform Fabrication Symposium, pp. 1-13.
Liravi et al., "A Hybrid Method for Additive Manufacturing of Silicone Structures," Solid Freeform Fabrication 2017: Proceedings of the 28th Annual International Solid Freeform Fabrication Symposium, pp. 1-21.
Toursangsaraki, "A Review of Multi-Material and Composite Parts Production by Modified Additive Manufacturing Methods", Jun. 12, 2018, pp. 1-25.
Unkovskiy et al., "Direct 3D Printing of Silicone Facial Prostheses: A Preliminary Experience in Digital Workflow," The Journal of Prosthetic Dentistry, Aug. 2018, pp. 1-6.
Coulter et al., "Production Techniques for 3D Printed Inflatable Elastomer Structures. Part 1—Fabricating Air-Permeable Forms and Coating with Inflatable Silicone Membranes via Spray Disposition", Mar. 2018, pp. 1-17.
Duoss et al., "Three-Dimensional Printing of Elastomeric, Cellular Architectures with Negative Stiffness," Advanced Functional Materials, vol. 24, 2014, pp. 4905-4913.

\* cited by examiner

ADDITIVE MANUFACTURING SYSTEM, METHOD AND CORRESPONDING COMPONENTS FOR MAKING ELASTOMERIC STRUCTURES

CROSS-REFERENCE TO RELATED APPLICATIONS

This application incorporates by reference co-pending U.S. application Ser. No. 16/680,959 entitled "MEDICAL DEVICE INCLUDING A STRUCTURE BASED ON FILAMENTS," by the certain inventors of this disclosure and filed on Nov. 12, 2019. This application also incorporates by reference U.S. provisional application No. 62/759,237, filed on Nov. 12, 2018, and 62/760,030, filed on Nov. 12, 2018.

FIELD OF THE DISCLOSURE

The disclosure relates to the field of additive manufacturing, and more particularly to an additive manufacturing system, method, and corresponding components for making structures based on filaments and elastomeric materials.

BACKGROUND

Additive manufacturing is an increasingly important manufacturing method, comprising numerous applications across many industries. Additive manufacturing, also known as "3D printing," is regarded as a transformative method for industrial production which facilitates the production of a three-dimensional article from a material according to a computer-aided design (CAD) of a definitive article by computer-aided manufacturing (CAM). In this sense, additive manufacturing is a digital revolution of analog manufacturing processes. Efforts have been made to apply additive manufacturing to articles formed from numerous types of materials, including polymeric materials, a subset of which are elastomeric materials.

Additive manufacturing of elastomeric materials, including silicone, are limited by several factors. In many existing systems, the fluidity of the elastomeric material requires the provision of a vat of liquid elastomeric material or precursor, in which a nozzle deposits curing agents to form a solid article from the liquid elastomeric material in situ, with leftover elastomeric material drained and washed away after the formation process is completed. Other additive manufacturing systems require a low- or room-temperature curing or vulcanizing elastomeric material so that the mass of elastomeric material quickly cures and does not deform during the formation process, as adding multiple layers of elastomeric material may not be accurately performed if the elastomeric material is uncured. Yet other additive manufacturing systems require that individual, discrete beads or droplets of elastomeric material are added one at a time to build a solid three-dimensional elastomeric structure from the base up.

Existing systems for elastomeric additive manufacturing, including those that utilize silicone, compromise the structural quality of the final product by using low viscosity, low-temperature-curing materials to enable the deposition process. It is not known in the art how to provide a smooth, consistent texture of deposited material having desired material properties. In medical applications, existing additive manufacturing systems preclude the additive manufacturing of medical-grade silicone, having the requisite strength, biocompatibility, and elasticity of conventionally manufactured medical products. Existing additive manufacturing systems have therefore been unable to meet the demand for articles made from medical-grade silicone that can exhibit the mechanical and chemical properties obtained from existing articles including medical devices formed by other, conventional manufacturing methods such as molding and extrusion.

In healthcare applications, silicone is a desirable elastomeric material due to its biocompatibility and long history of implanted medical devices. Due to confirmatory biological testing, use of existing medical-grade silicone materials is desirable to reduce the time from concept to market. Despite its accepted use in healthcare applications, silicone materials are thick and viscous and require high pressure to be injected into molds to manufacture a precise article, such as through injection molding and transfer molding processes. Challenges are imposed in additive manufacturing because it is difficult to precisely extrude significantly viscous silicone onto a substrate into a definitive shape with high pressure if no mold is employed, while accounting for curing and shrinkage rates, as the silicone often deforms, sags, or otherwise loses its desired shape before curing.

While silicone materials can be processed and formed in small batches in a design phase, difficulties arise when scaling up production of silicone as not only is its viscosity difficult to manage, but other factors must be considered including curing temperature and time, entrapment of air or bubbles, shrinkage, mixture of parts, and cross-linking to manufacture medically-accepted articles. Silicone is a thermoset polymeric material and will cure into its given shape of a strong, dimensionally stable and heat- and chemical-resistant article, but such advantages also require that the structure into which the silicone cures must be made correctly at the onset as later adaptation is typically not feasible. This limits the customizability of elastomeric structures formed through additive manufacturing. Any additive manufacturing process on a commercially scalable level should be able to preserve the mechanical properties of a cured silicone, such as toughness and elasticity and other properties desirable in a medical-grade silicone article while offering high throughput and precision.

Existing systems for additive manufacturing may provide for only a monolithic or single-property structure, as only a single grade or blend of material can be deposited. The structures and functions of additive-manufactured articles are limited to what can be achieved through a single material property. There is a need for an additive manufacturing system that can accurately deposit material having different properties to attain a final product with desired properties in desired regions.

Another problem of existing manufacturing systems is that many are limited to depositing a single discrete bead of elastomeric material at a time, limiting the construction of 3D-printed articles to discontinuous structures that are a sum of individual drops or beads, rather than comprising smooth and continuous layers, filaments, or structures with varying properties.

Many production and manufacturing methods are limited to providing a mold in which elastomeric material may be injected and thereafter cured to attain a desired shape and properties. This considerably limits the design and manufacturing flexibility when preparing an article. Because existing methods are limited to processes that deposit discrete beads or inject elastomeric material into negative molds, there is a need for a system that can deposit filaments of elastomeric material to form a structure with desired properties at desired locations.

Existing systems are directed to implementations where an article is built from the bottom up and only in cartesian coordinates. In other systems, the effects of gravity on uncured or partially cured polymer materials limit the dimensions of the article, as too much material added to the article causes distortions from gravity, particularly combined with the effects of viscosity and curing rates as discussed above. There is a need for an additive manufacturing system that overcomes the effects of gravity and allows for additive manufacturing of articles in multiple dimensions.

Solutions that attempt to perform additive manufacturing on a rotating build surface or substrate do not provide for the additive manufacturing of medical-grade silicones, which require particular viscosities and cure rates, but rather as limited to systems that utilize shavers or cutters that remove extra, unwanted deposited material. These systems also are configured to allow material to drip or fall away from the substrate. There is no teaching of using a rotating substrate that achieves desired printing of medical-grade structures from silicone without cutters and dripping configurations to conductive negative manufacturing procedures.

There is a need for an additive manufacturing system that overcomes the limitations of existing systems, namely that low-quality elastomeric materials are used to enable deposition limited to depositing discrete beads, that properties of materials are monolithic and cannot be dynamic to account for different structural and functional needs at different parts or components of an elastomeric additive-manufactured article, and that the methods for additive manufacturing are limited to bottom-up approaches, with gravity effects unmitigated and unaddressed. It is highly desirable to use known silicone materials having confirmatory biological testing in additive manufacturing to create precise silicone-based structures suitable for medical devices.

SUMMARY

The additive manufacturing system, method and corresponding components for making silicone structures of the disclosure advantageously provides a system for providing material in desired quantities and at desired locations of an article with an improved dispensing and deposition apparatus, resulting in smooth, continuous depositions of beads, filaments, or layers of material with controlled variation of desired properties and at desired locations. The additive manufacturing system of the disclosure may comprise three primary dispensing systems, including a first dispensing system, a secondary dispensing system, and a deposition apparatus. The additive manufacturing system may further comprise a deposition substrate arranged to cooperate with the three primary dispensing systems.

The first dispensing system may comprise a vat or reservoir of at least one additive manufacturing material, the material arranged to be drawn from the vat or reservoir, and transmitted to the secondary dispensing system as the additive manufacturing system forms an article from the material. A separate vat or reservoir may correspond to different materials. Silicone is often of a two-part, 1:1 mix ratio material preferably drawn from at least two reservoirs, although more reservoirs may create different combinations of silicone compositions with desired properties at desired locations of an additively manufactured article.

A secondary dispensing system may comprise a proportioning column or device and control valves arranged to correspond to or cooperate with the respective vat or reservoir of the first dispensing system. The proportioning column preferably draws the material from the reservoir and stores it in a volume of the proportioning column. The control valves associated with the proportioning column are arranged to control a rate and volume according to which the material is stored in the proportioning column and at which it may be transmitted towards the deposition apparatus. A plurality of proportioning columns and corresponding control valves may be provided and may each correspond to a respective vat or reservoir in the first dispensing system, with each of the proportioning columns, control valves, and vats containing different materials or blends of materials selected and proportioned to impart desired properties to the final article.

The deposition apparatus is arranged to receive the material from the proportioning column in rates and volumes that correspond to properties desired at specific locations along with an article being formed. The deposition apparatus comprises a dynamic mixer to blend the material, which as discussed may comprise two or more components or separate parts blended before being deposited.

The deposition apparatus may have a modular construction and comprise heat transfer components, sonic vibration components, pneumatic stop valves, and other modules as may enable a smooth, consistent deposition of the material while varying desired properties. A nozzle may be provided for depositing the material onto the article.

A deposition substrate may be arranged to cooperate with the additive manufacturing system. The deposition substrate may comprise a moving substrate on which the material may be deposited and cured. The moving substrate may counteract or overcome the effects of gravity on the deposited material, thereby keeping it in a desired dimensional state as it cures. The deposition substrate allows for forming an article with desired features and properties in desired locations in different paths or orders than are available in existing additive manufacturing systems, particularly for materials like medical-grade silicone. The deposition substrate may comprise heat transfer components for tailoring the cure rate of the deposited material and improving the process of deposition as the material may better retain a desired shape and configuration.

These and other features of the present disclosure will become better understood regarding the following description, appended claims, and accompanying drawings.

Figure 1:
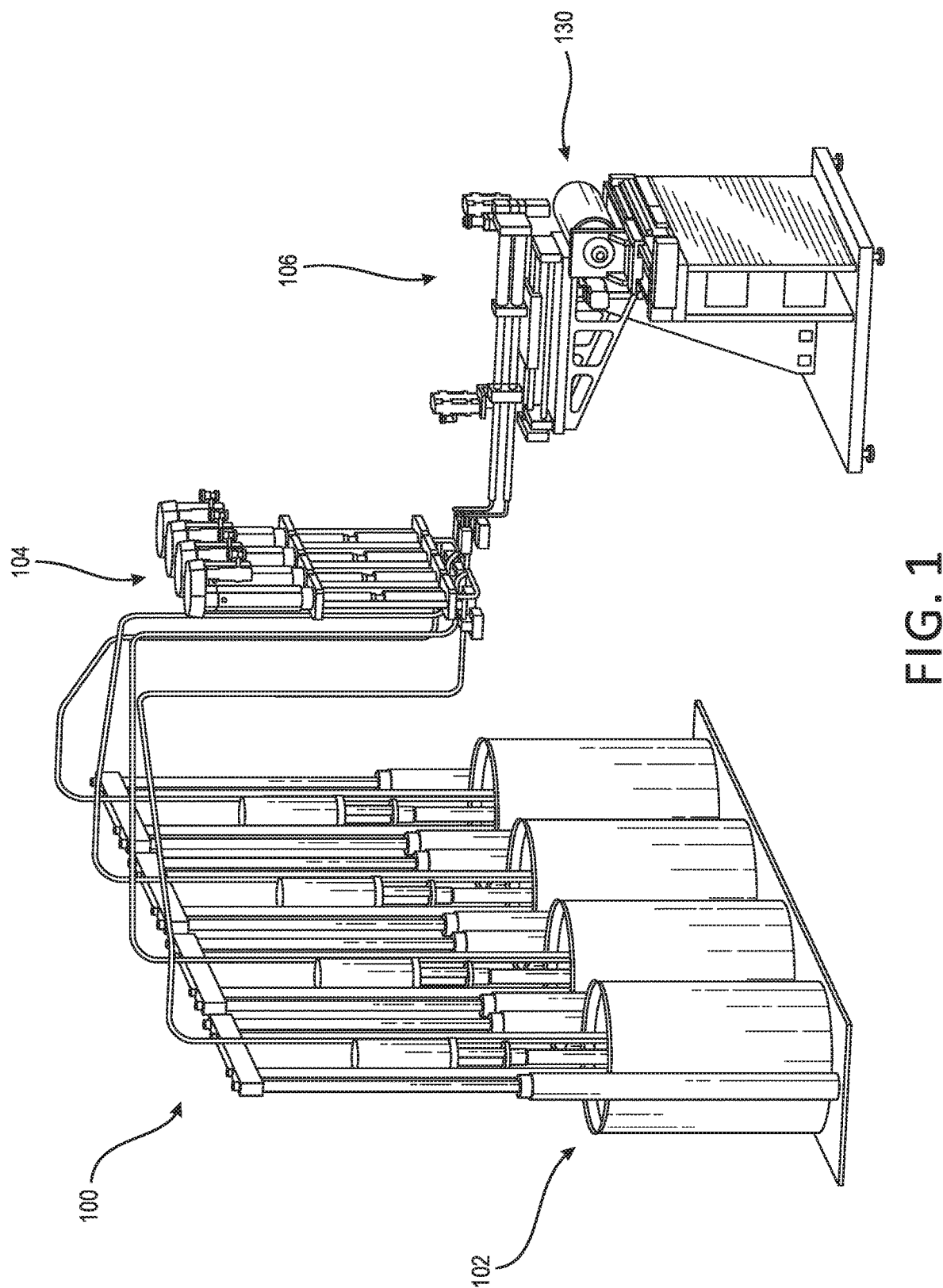
FIG. 1 is a perspective view of an additive manufacturing system according to an embodiment.

The drawing figures are not necessarily drawn to scale, but instead are drawn to provide a better understanding of the components, and are not intended to be limiting in scope, but to provide exemplary illustrations. The figures illustrate exemplary configurations of an additive manufacturing system, and in no way limit the structures or configurations of the additive manufacturing system, methods, and corresponding components according to the present disclosure.

DETAILED DESCRIPTION OF VARIOUS EMBODIMENTS

The additive manufacturing system, method, and corresponding components for making elastomeric structures of the disclosure address the limitations of existing additive manufacturing systems by providing a first dispensing system, a secondary dispensing system, and a deposition apparatus according to embodiments of the disclosure. The additive manufacturing system achieves controlled variability of material properties throughout a produced article, with a dynamic mixing apparatus that creates smooth, consistent material blends for precise, discrete and/or continuous deposits of material such as filaments of elastomeric material that chemically bond together to define an elastomeric 3D-printed article. A dynamic deposition substrate may be arranged for cooperating with the deposition apparatus to overcome the effects of gravity and to facilitate dynamic orders or paths of additive manufacturing. Combinations of these components may be provided with other known components, and do not have to be used in combination with one another.

Structures that can be manufactured according to the system, methods, and components thereof are described in co-pending U.S. application Ser. No. 16/680,959 entitled "MEDICAL DEVICE INCLUDING A STRUCTURE BASED ON FILAMENTS," by certain inventors of this disclosure, and concurrently filed on Nov. 12, 2019.

The Applicant incorporates herein by reference the "6$^{th}$ Edition Silicone Design Manual by Albright Technologies Inc.," at www.Albright1.com, and retrieved on Nov. 8, 2018, published by Albright Technologies of Leominster, Mass., U.S.A.

FIG. 1 depicts in perspective view an additive manufacturing system 100 according to an embodiment of the disclosure. A first dispensing system 102 comprises vats or reservoirs containing at least one material and is connected to a secondary dispensing system 104, which provides material from the first dispensing system 102 to a deposition apparatus 106 in desired proportions. The additive manufacturing system 100 may be arranged to cooperate with a deposition substrate 130, as will be described further herein.

Examples of medical-grade elastomer that may be utilized by the additive manufacturing system 100 include silicone, polyurethane, or other elastomeric materials. For the disclosure, the embodiments will be described as formed from medical-grade silicone. An example of a medical-grade silicone is obtainable from NuSil Technology of Carpinteria, Calif., under product designations MED-4901, MED-6340, or MED-6345, although other silicone compositions can be used.

Figure 2:
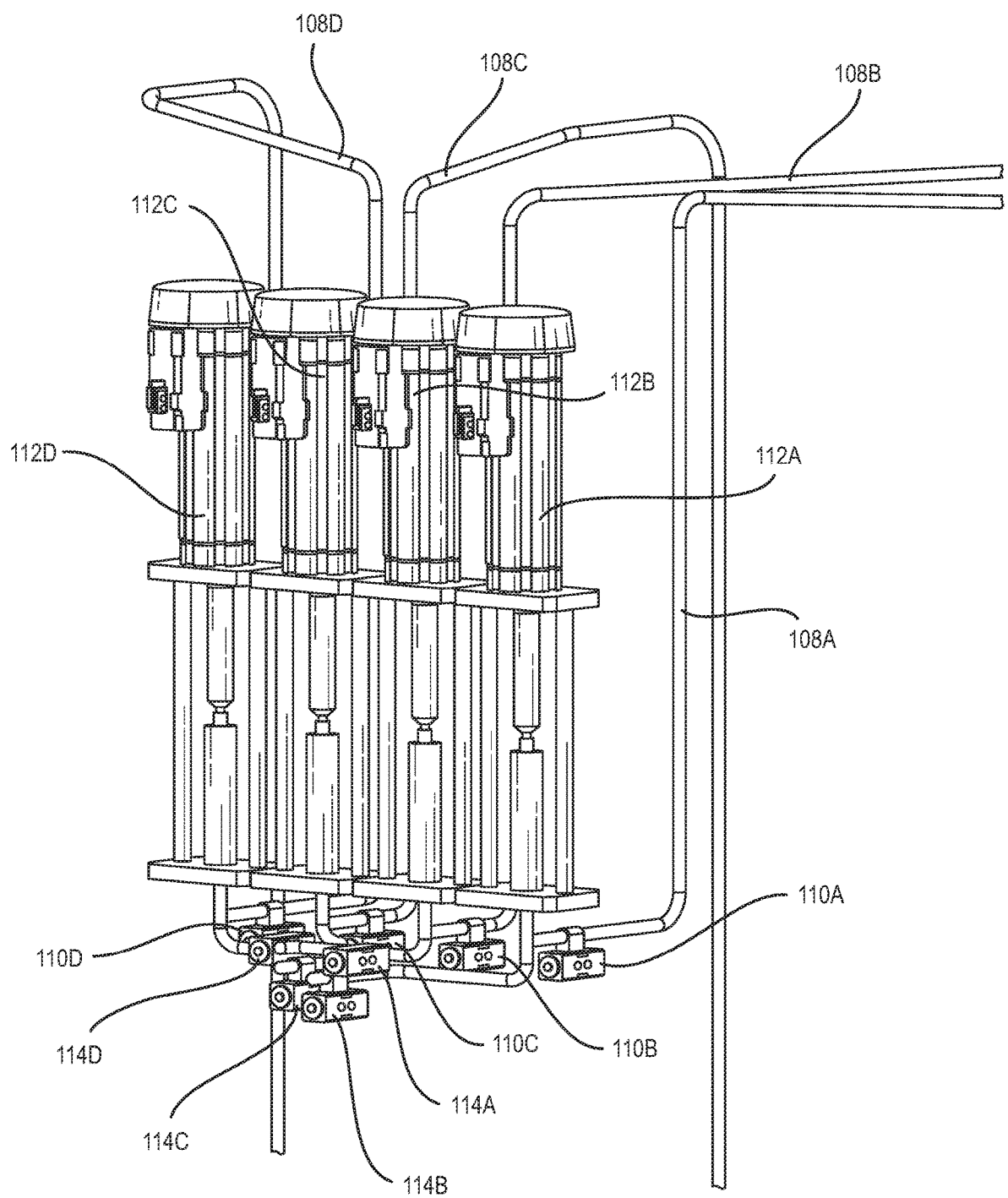
FIG. 2 is a perspective view of a secondary dispensing system of the additive manufacturing system of FIG. 1.

FIG. 2 is a perspective view of a secondary dispensing system 104, as shown in the embodiment of FIG. 1. The secondary dispensing system 104 comprises a plurality of proportioning columns or devices 112A, 112B, 112C, 112D. Each of the proportioning columns 112A, 112B, 112C, 112D is connected to a corresponding vat or reservoir in the first dispensing system 102 via a respective reservoir feed line 108A, 108B, 108C, 108D. Elastomeric material, additives, pigments, crosslinking agents, curing agents, or any other suitable component may be provided from the reservoirs in the first dispensing system 102 to the secondary dispensing system 104 via the reservoir feed lines 108A, 108B, 108C, 108D. In embodiments, the elastomeric material may be liquid silicone material comprising two parts, which may be cured to form a solid silicone structure.

The proportioning columns 112A, 112B, 112C, 112D may be configured to receive within an interior volume thereof (not shown) a quantity of material or other material from the vats or reservoirs in the first dispensing system 102, and to distribute the material via respective proportioning control valves 114A, 114B, 114C, 114D toward the deposition apparatus 106. The proportioning columns 112A, 112B, 112C, 112D may draw the material from the vats in the first dispensing system 102 in a controlled manner via receiving control valves 110A, 110B, 110C, 110D. The receiving control valves 110A, 110B, 110C, 110D are arranged to maintain a specified volume of material in the proportioning columns 112A, 112B, 112C, 112D and/or to provide a required amount of material based on the deposition process downstream of the proportioning columns 112A, 112B, 112C, 112D.

The receiving control valves 110A, 110B, 110C, 110D may be servo-controlled or otherwise controlled, and are arranged to communicate with a controller. The controller may comprise a mathematical model and/or a process control scheme to direct the receiving control valves 110A-D and the proportioning control valves 114A, 114B, 114C, 114D to open and transmit the material in the interior volume of the proportioning columns or devices 112A, 112B, 112C, 112D to the deposition apparatus 106 in desired proportions to effect desired properties at desired locations in the article.

By providing the controller in communication with the proportioning control valves 114A, 114B, 114C, 114D, desired amounts of material types, including the two parts of a liquid silicone material, or other additives, may be provided at specific times corresponding to a moment during a deposition process at which the deposition apparatus 106 will deposit the material or additives at a desired location on the formed article. As the proportioning columns 112A, 112B, 112C, 112D, and respective proportioning control valves 114A, 114B, 114C, 114D act simultaneously and cooperatively, infinitely many combinations of the two parts of the liquid silicone material and other additives may be defined, providing the formed article with precise combinations of material to form continuous sections, features, and components having desired properties and without interruption to the flow of the material through system 100, as opposed to the monolithic articles formed by existing methods of additive manufacturing or by methods such as injection molding, which have unvarying properties throughout the articles.

For example, the secondary dispensing system 104 may be arranged to create material blends comprising elastomeric polymeric materials, such as parts A and B of a two-part silicone material mix, and additives that may influence the cure times of the material blend, the cure temperature of the material blend, color, stiffness, strength, elasticity, or any other property of particular regions of the final article. The secondary dispensing system 104 advantageously may provide elastomeric materials and additives in any proportions needed, so infinitely many combinations of properties may be attained and at desired locations along with the article.

While in the embodiment of FIG. 2, only four proportioning columns 112A, 112B, 112C, 112D are depicted, it will be appreciated that fewer or more proportioning columns may be utilized as deemed suitable. For example, in large or complex articles, more proportioning columns may be provided to supply additional specialized additives or different types of polymeric materials. For example, silicone oils may be provided for adjusting a durometer of certain materials, accelerators may be provided to adjust cure times, and other agents or additives may be provided for fine-tuning the properties of the final materials in the article. Redundant vats or proportioning columns may be provided to facilitate continuous deposition of the article when a particular vat or proportioning column runs out of a material part.

Figure 3:
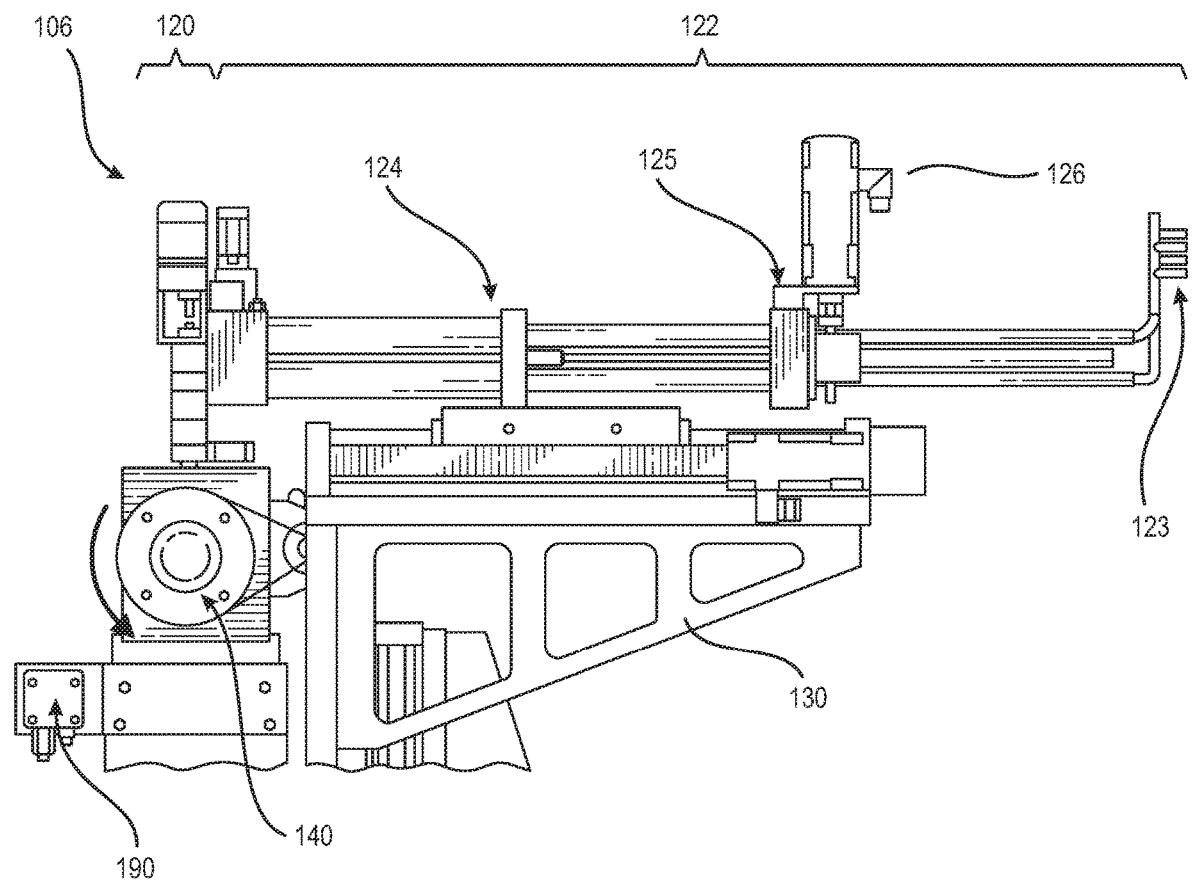
FIG. 3 is an elevational view of a deposition apparatus of the additive manufacturing system of FIG. 1.

FIG. 3 is an elevational view of a deposition apparatus 106 according to the embodiment of the additive manufacturing system 100 introduced in FIG. 1. The deposition apparatus 106 may comprise a deposition head 120 and a feed component 122, the deposition head 120 controlling the deposition of material onto an article, and the feed component 122 controlling a rate and quantity at which material is fed from the secondary dispensing system 104 to the deposition head 120. The feed component 122 may comprise a material inlet 123 configured to receive material at or from the proportioning control valves 114A, 114B, 114C, 114D. The feed component 122 may be mounted on a rack 130 relative to the deposition head 120, facilitating movement of a displacement pump 124 to conduct material towards the deposition head 120. An actuator 140 may be arranged to translate the displacement pump 124 or to translate the deposition head 120 in the desired direction. A nozzle 190 deposits the material onto an article being formed.

Material is configured to be received from the secondary dispensing system 104 at a displacement pump head 125 via a displacement pump control valve 126. The displacement pump 124 ultimately conducts the material from the displacement pump head 125 towards the deposition head 120. The control valve 126 advantageously is configured to conduct the material in a first-in, first-out manner; that is, the material is moved to the deposition head 120 in the order in which it was conducted from the secondary dispensing system 104, retaining its properties and sequential order of dispense. This allows the properties of the printed article to be controlled all the way back to the receiving control valves 110A-D and the respective reservoirs of the primary dispensing system 102, improving the particularity of the control of the process and the efficiency of resource consumption.

Figure 4:
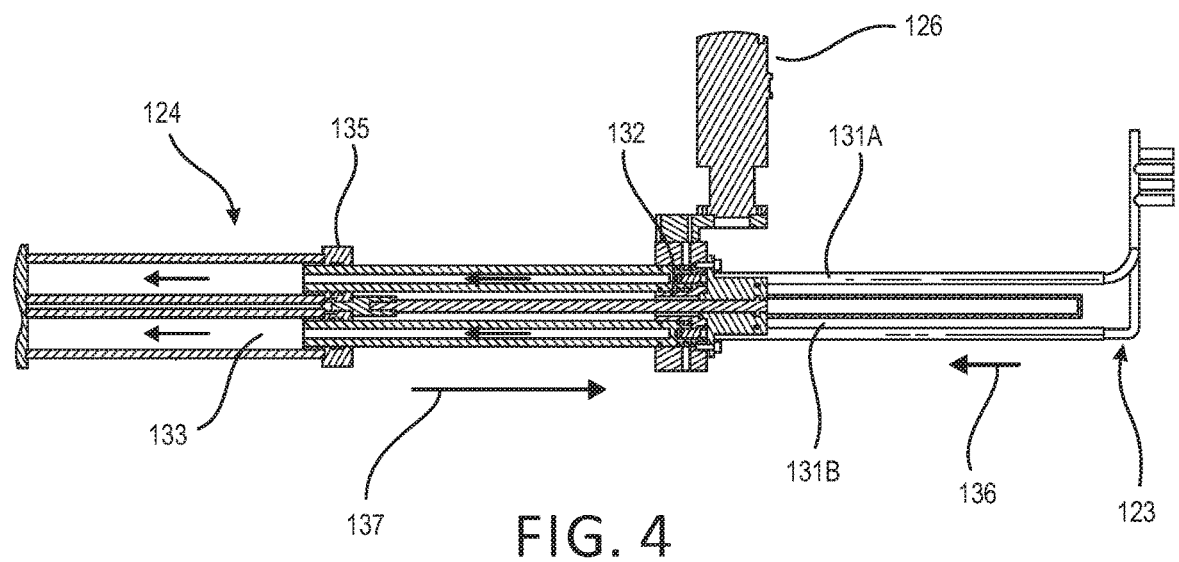
FIG. 4 is a cutaway elevational view of a material flow portion of the additive manufacturing system of FIG. 1.

The displacement pump 124 may comprise a piston pump, with an outer component and an inner component concentric with, the interior of, and/or adjacent to the outer component. As seen in greater detail in the cutaway elevational view of FIG. 4, material may flow or be conducted from the secondary dispensing system 104 in a flow direction 136 in first and second material inlets 131A, 131B, corresponding respectively to parts A and B of an uncured or unpolymerized elastomeric material, in an exemplary embodiment a two-part silicone material. The material is conducted in the separate first and second material inlets 131A, 131B to facilitate fluid flow uninterrupted by formation of elastomer solids. The actuator 126 is arranged to conduct the material in a first-in, first-out manner through the displacement pump head 125 into a material fill port 132 arranged at the inner component of the displacement pump 124.

As the material accumulates through the material fill port 132 in the inner component of the displacement pump 124, piston rods 135 are guided backward in a direction 137 towards the displacement pump head 125. The piston rods 135 are configured to receive accumulated material in an interior volume thereof without blending or otherwise affecting the order of the accumulated material. As the piston rods 135 are driven outward toward the deposition head 120, the accumulated material is conducted toward the deposition head 120 in the same order in which it was received at the displacement pump 124 from the secondary dispensing system 104, such that materials having desired properties will be deposited at the desired locations on the article.

Figure 5A:
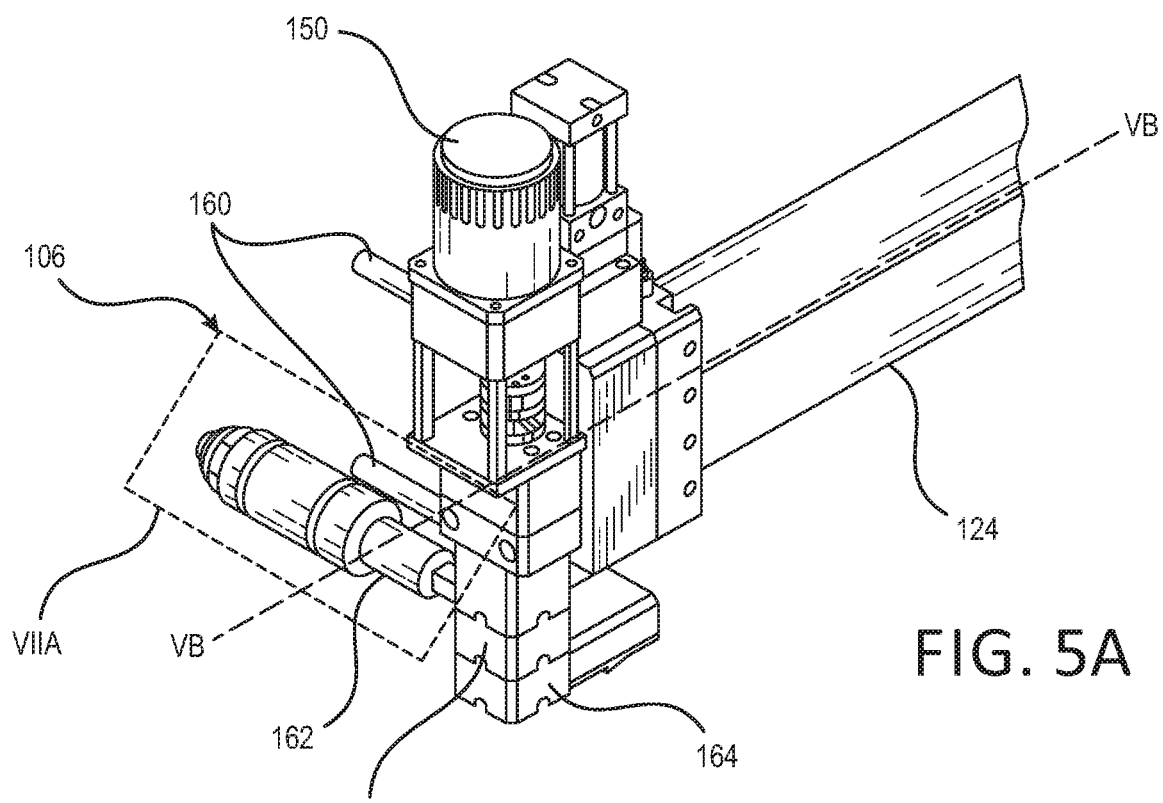
FIG. 5A is a perspective view of a deposition apparatus of the additive manufacturing system of FIG. 1.
Figure 5B:
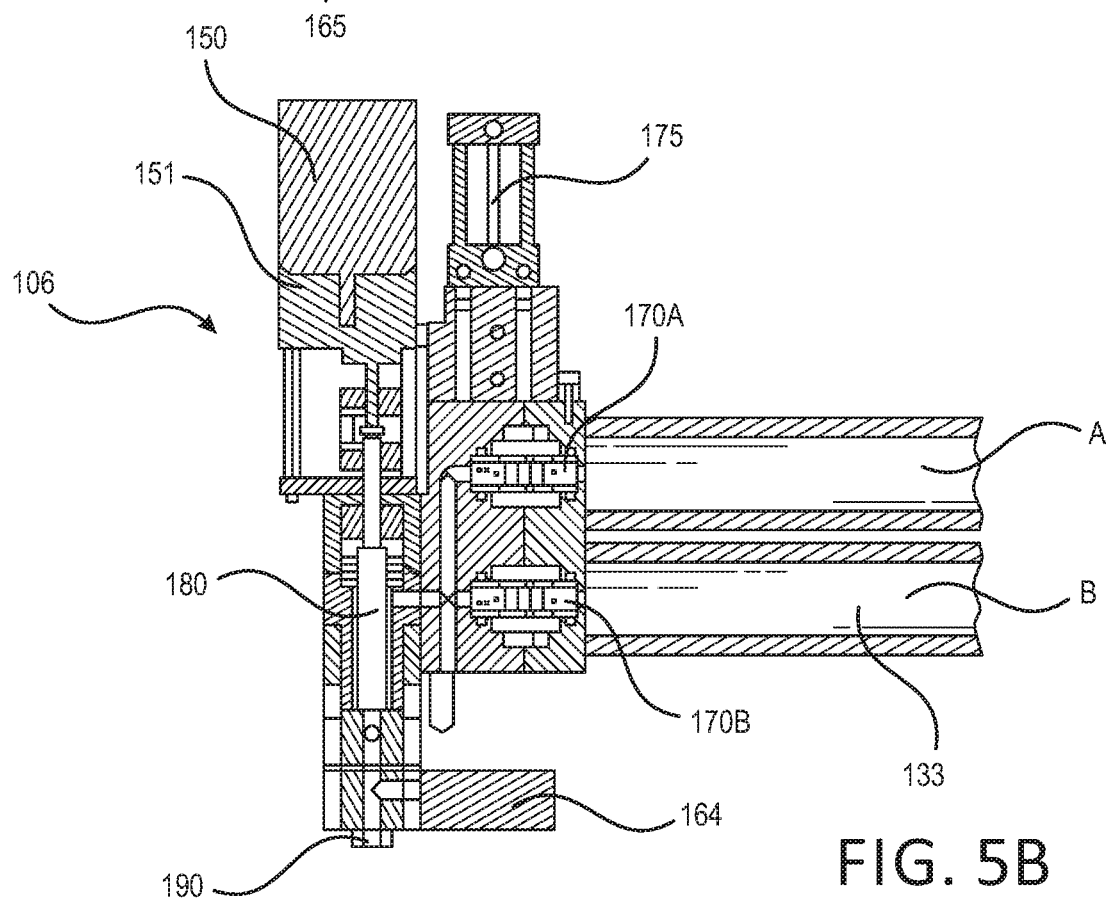
FIG. 5B is an elevational cross-sectional view of the deposition apparatus of FIG. 5A taken along the line VB-VB.

The displacement pump 124 conducts the material towards the deposition head 120 of the deposition apparatus 106. As seen in FIGS. 5A and 5B, the deposition head 120 may comprise a dynamic mixing module 150 configured to both actuate and blend the material, such as parts A and B of two-part silicone material, preparatory to depositing the blended material on the substrate to form the article. The deposition head 120 may further comprise a heat transfer module 160, which facilitates heating or cooling of a block forming the deposition head 120. A pneumatic suck-back or stop valve 162 is provided proximate a nozzle 190 to achieve a clean cut-off of blended material after a discrete portion of material has been deposited on the article.

In embodiments, the pneumatic suck-back valve 162 may be arranged to define distinct filaments of a plurality of filaments that together form a 3D-printed article. As the deposition head 120 deposits material at different portions of an article, the pneumatic suck-back valve 162 may be actuated to retract or withdraw the material in the deposition head away from the nozzle 190 to facilitate a clean break between the distinct filaments or portions of the article. The deposition thereby avoids the problem of strings of material forming or smearing throughout the article. Whereas existing printheads reverse a flow direction of the material to enact a suck-back by reversing a rotation of an impeller, as discussed in greater detail below, the pneumatic suck-back valve 162 of embodiments of the disclosure utilizes instead a piston arrangement that creates a vacuum effect to withdraw as desired the material away from the nozzle, creating clean breaks to distinguish individual filaments, beads, or layers of printed material.

Additional mixer or valve modules may be advantageously added to the deposition head 120 as desired. For instance, a sonic vibration module 164 is provided proximate the nozzle 190 to provide an additional blending procedure, for example, to reduce a viscosity of the blended material and/or to activate certain additives in the material. The deposition apparatus 106 may advantageously be configured as a modular assembly to be easily dissembled and reassembled for easy cleaning and/or for interchange of individual components based on the needs of a particular task. Where additional vibration, heat transfer, or suck-back modules are required, for example, such may be easily added to and later removed from the deposition head 120.

Scorelines may be provided at grooves and/or between individual modules in the deposition apparatus 106, or anywhere along with the additive manufacturing system 100, where leakage of material from inside the additive manufacturing system 100 is encouraged, the leakage facilitating the expulsion of contaminants from the material. This may be utilized especially in high-purity applications such as producing medical-grade silicones, where contaminants are unsuitable for use with the human body.

Turning to FIG. 5B, the dynamic mixing module 150 may comprise an impeller 180 configured to dynamically mix material obtained from first and second control valves 170A, 170B, the first and second control valves 170A, 170B arranged to conduct and dispense material from the displacement pump 124 according to a desired final blend of material. A control valve actuator 175 may be arranged to communicate with the controller and to independently actuate the first and second control valves 170A, 170B based on the desired material property at a desired location along the article. The first and second control valves 170A, 170B may correspond to parts A and B of a two-part silicone material or otherwise can correspond to respective proportioning devices of the secondary dispensing system 104.

Figure 6:
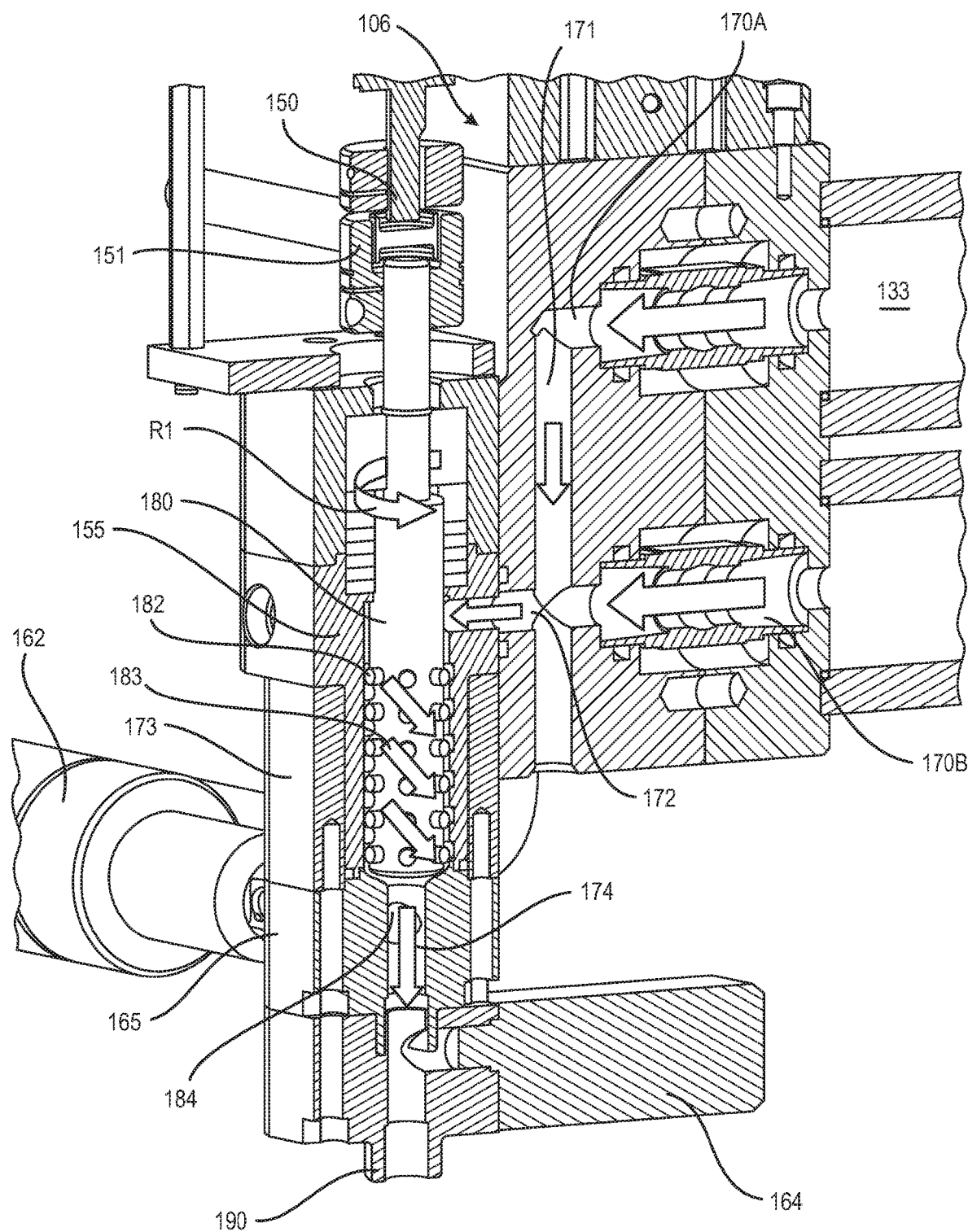
FIG. 6 is a perspective cutaway view of the deposition apparatus of FIG. 5A.

The cutaway perspective view of the deposition apparatus 106 shown in FIG. 6 illustrates the operation of the deposition head 120 on received material. As the material is obtained from an interior volume 133 of the displacement pump 124, the control valves 170A, 170B control the rate and volume at which the material, in this embodiment provided in two parts A and B, may advance toward the dynamic mixing module 150. As material part A passes the control valve 170A, it is conducted along a flow direction 171 toward the material part B provided from the control valve 170B, and then both parts A and B may advance in a combined but unblended flow at a flow direction 172 toward the dynamic mixing module 150.

The impeller 180 is driven by an actuator 151 to rotate in a direction R1, with protrusions 182 actuating downward flow of the combined but unblended material parts A and B. As parts A and B flow through dynamic flow paths 183 defined by and between the protrusions 182, parts A and B are blended to obtain a smooth and consistent material mixture. In an exemplary embodiment, the dynamic mixing module 150 advantageously removes air bubbles from the material, facilitating a more structurally solid, smooth, and aesthetically pleasing formed article. The generally downward flow paths 183 thus conduct the material in a flow direction 173 towards the nozzle 190. The impeller 180 further is arranged to keep the pressure constant, which improves flow and consistency.

As the blended material passes by a distal end of the impeller 180, the blended material passes along a flow direction 174 toward the nozzle 190. A sonic vibration module 164 may provide additional blending and may advantageously reduce the viscosity of the blended material immediately prior to deposition when desired, for example to increase an amount of material deposited at a particular location. In embodiments, certain additives contained in the blended material may be arranged to activate or change properties upon receiving sonic vibrations at the sonic vibration module 164, thereby enhancing properties of the blended material immediately before deposition.

Figure 7A:
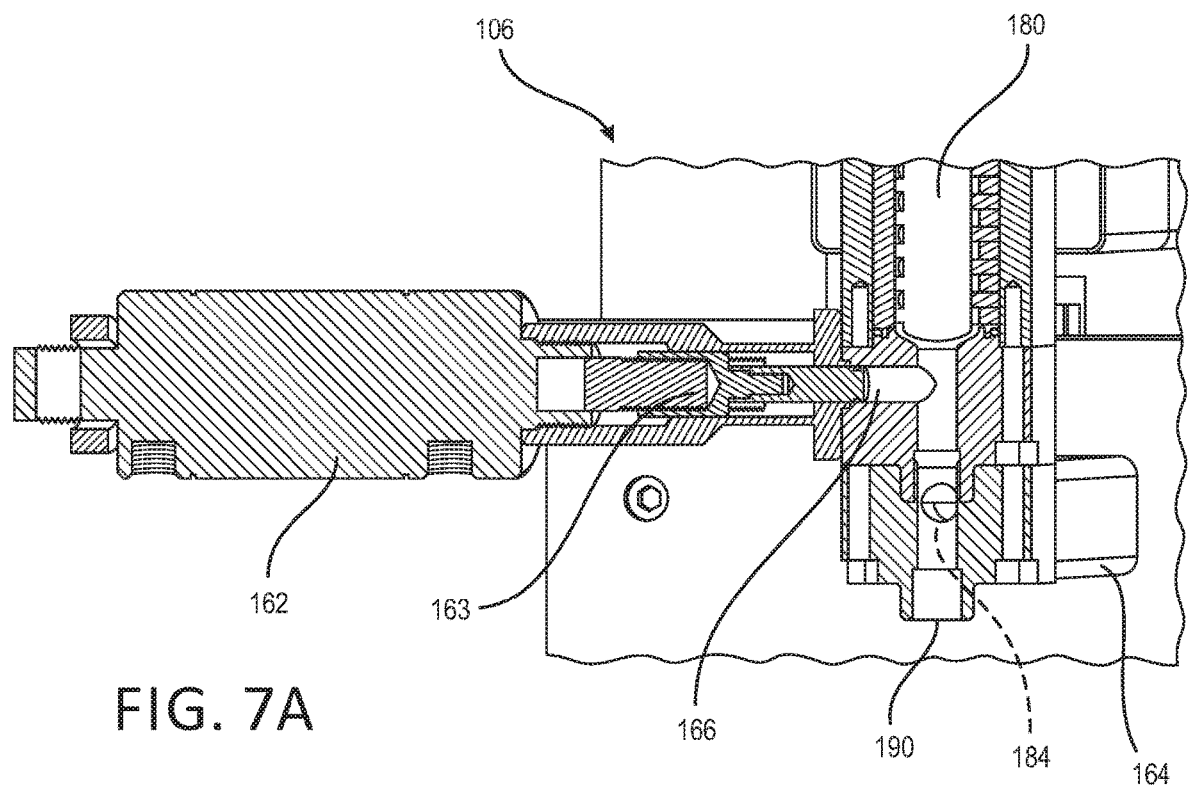
FIG. 7A is a cutaway detail view VIIA of the pneumatic valve assembly of the deposition apparatus of FIG. 5A.

The pneumatic suck-back or stop valve 162, as seen more clearly in the cutaway elevational view of FIG. 7A provides a clean cut-off of the blended material, operating to temporarily arrest the flow of the blended material along the flow path 174 by providing a negative pressure that draws blended material back up a distance in the flow channel 184, thereby preventing unwanted deposition, smearing, or dripping of blended material from the nozzle 190. As discussed, this may be particularly advantageous when defining distinct filaments of material and/or at distinct points on the printed article.

The pneumatic suck-back valve 162 comprises a plunger 163 configured by operation of a driver to sharply withdraw away from the flow channel 184, creating a negative pressure in a pneumatic stop line 166 that draws the blended material back upwardly from the nozzle 190, toward which the blended material otherwise flows due to the actuation of the impeller 180 and in certain configurations due to gravity and back pressure applied from the displacement pump 124. The negative pressure can be released as the plunger 163 is released by the driver and allowed to return to its original configuration, and the flow of the blended material along the flow path 174 is reestablished.

The arrangement of the pneumatic suck-back valve 162 with the plunger 163 facilitates retraction of material and clean breaks between distinct drops, filaments, or layers without requiring that the actuator 151 reverse its rotation in order to create the retraction. Whereas existing printheads utilize reverse-flow to retract material, the operation of the dynamic mixing module 150 is simplified, and wear and tear on the actuator 151, and the impeller 180 are minimized, by the provision of the modular pneumatic suck-back valve 162.

In embodiments, the pneumatic suck-back valve 162 can operate to define apertures in a layer, film, filament, or other deposit of material with high precision. As the deposition apparatus 106 lays down or deposits an otherwise continuous layer or filament of material, the pneumatic suck-back valve 162 may interrupt the deposition for a controlled amount of time to define a gap or aperture in the continuous layer or filament.

The pneumatic suck-back valve 162 may be particularly active and advantageous during stages of deposition where the deposition head 120 is changing a direction along the substrate. For example, the deposition head 120 and the substrate may be arranged to move relative to each other such that the deposition head 120 and the nozzle 190 travel along a surface of the substrate and deposit a continuous filament thereon while additively manufacturing the article. As the deposition head 120 so travels and deposits the continuous filament, the deposition head 120 and the substrate may change a direction of travel, defining an edge or corner portion of the article, or otherwise defining a break in a continuous filament. The pneumatic suck-back valve 162 may, at the moment that the direction of travel is changed, activate to retract the material flowing through the flow path 174 to effect a clean break distinguishing the filament or material deposited along the surface of the substrate. The pneumatic suck-back valve 162, as depicted and described is merely exemplary, and other suitable methods, components, and arrangements are envisioned for providing a clean cut-off of material at the nozzle 190.

The nozzle 190 may comprise any configuration or size for varied and controlled deposition of material. In certain embodiments, the nozzle 190 may have a larger diameter configured to deposit discrete beads or continuous layers of material, while in other embodiments, the nozzle 190 may have a nozzle configured for depositing a continuous filament. The nozzle 190 may have a circular diameter or may comprise a textured aperture allowing for depositions of beads, layers, or filaments having desired textural features. The nozzle 190 may have a dynamic size and/or shape, and can change during deposition to form different sized and shaped deposits. In embodiments, the nozzle 190 may be sized to allow for concentric or coaxial arrangements and flows of different materials, as described in greater detail below.

In embodiments, the nozzle 190 has a same size throughout the course of additively manufacturing a single article. The thread diameters of the layers and/or filaments deposited by the nozzle 190 can be adjusted by controlling the proportions of the print speed, i.e. the flow rate of the material through the deposition head 120, and the material dispense rate, i.e. the flow rate of material from and through the first and second dispensing systems 102, 104. This allows for variable thicknesses and stiffnesses throughout the printed article while continuing the continuous print layers from a single size nozzle 190.

Figure 7B:
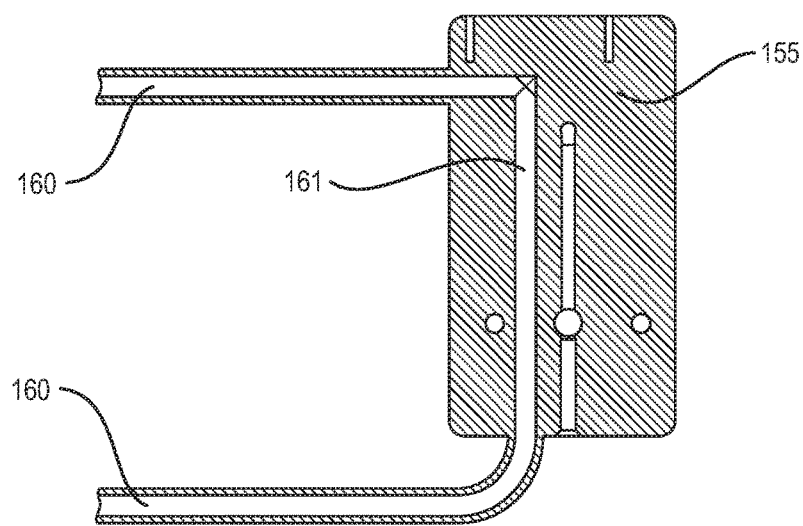
FIG. 7B is a cutaway elevational view of a heat transfer system in an embodiment of a deposition apparatus of an additive manufacturing system according to the disclosure.

FIG. 7B illustrates the operation of the heat transfer module 160. A heat transfer medium or fluid is conducted through at least one heat transfer line 161 along a flow path 166 within a block 155, defining at least partially the deposition head 120. The block 155 may be formed from aluminum, stainless steel, Teflon, polymers, or any other suitable material that provides sufficient mechanical support, material purity, and/or heat-transfer characteristics. The material forming the block 155 may advantageously be chosen for minimizing contamination of the material flowing therethrough, this arrangement facilitating the use and production of medical-grade elastomeric articles.

In certain embodiments, the heat transfer fluid may be a refrigerant or other cooling fluid such as cooling water arranged to reduce a temperature of the block 155 and consequently of the material flowing through flow channels 171, 172, 173, 174 defined therein. This may be particularly advantageous for low temperature-curing materials, the cooling effects preventing premature polymerization. In other embodiments, the heat transfer medium may be arranged to add heat to the block 155, for example, to increase a property such as viscosity of the material flowing through the block 155.

The heat-transfer module 160 may be controlled manually or by the controller based on information obtained through temperature and/or pressure sensors arranged throughout the deposition apparatus 106. For example, a downstream temperature of the blended material exiting the dynamic mixing module 150 may trigger, based on a process control scheme according to the calculated properties of the blended material, a need for temperature reduction in the block 155. The heat-transfer module 160 may communicate with the controller to automatically increase a flow rate of a cooling fluid to decrease the temperature of the block 155, and consequently of the blended material exiting the dynamic mixing module 150.

In embodiments, the controller may indicate or determine that a temperature in the block 155 should be increased to, for example, increase temperature and decrease viscosity of the material. This may be beneficial when the flowrate and deposition rate needs to be increased at a particular location for increased thickness or rigidity of particular filaments or segments. In embodiments where the heat-transfer module 160 is a cooling module, the flowrate of cooling heat-transfer fluid or medium (such as cooling water) may be correspondingly decreased; conversely, when the heat-transfer module 160 is a heating module, the flowrate of heating fluid or power may be correspondingly increased.

When arranged as a heating module, the heat-transfer module 160 may utilize any suitable heating element, including heated fluids arranged to flow through the at least one heat-transfer line 161, electric heating elements arranged to extend through a thickness of the block 155, or any other suitable arrangement or component. The heat-transfer module 160 may be arranged to transfer heat from discrete portions of the block 155 or any portion of the deposition head 120 at different times; for example, the heat-transfer module 160 may provide head upstream of and proximate the impeller 180 while removing heat proximate the nozzle 190. In other embodiments, the heat-transfer module 160 may remove heat proximate the impeller 180 to prevent any undesired curing in the deposition head 120. The heat transfer performed by the heat-transfer module 160 may be dynamic and can vary based on the composition of the material flowing through the deposition head 120 at any given time.

Likewise, the pressure of the material may be monitored via pressure sensors at any number of locations in the additive manufacturing system 100. The controller may be arranged to detect a pressure at an outlet of, for example, the dynamic mixing module 150, the displacement pump 124, or the nozzle 190, with adjustments made at the displacement pump 124, the control valves 170A, 170B, and/or the control valves 114A, 114B, 114C, 114D of the secondary dispensing system, for example, to maintain a proper pressure of the material throughout the additive manufacturing system 100 and to optimize the flow characteristics of the material.

Figure 8:
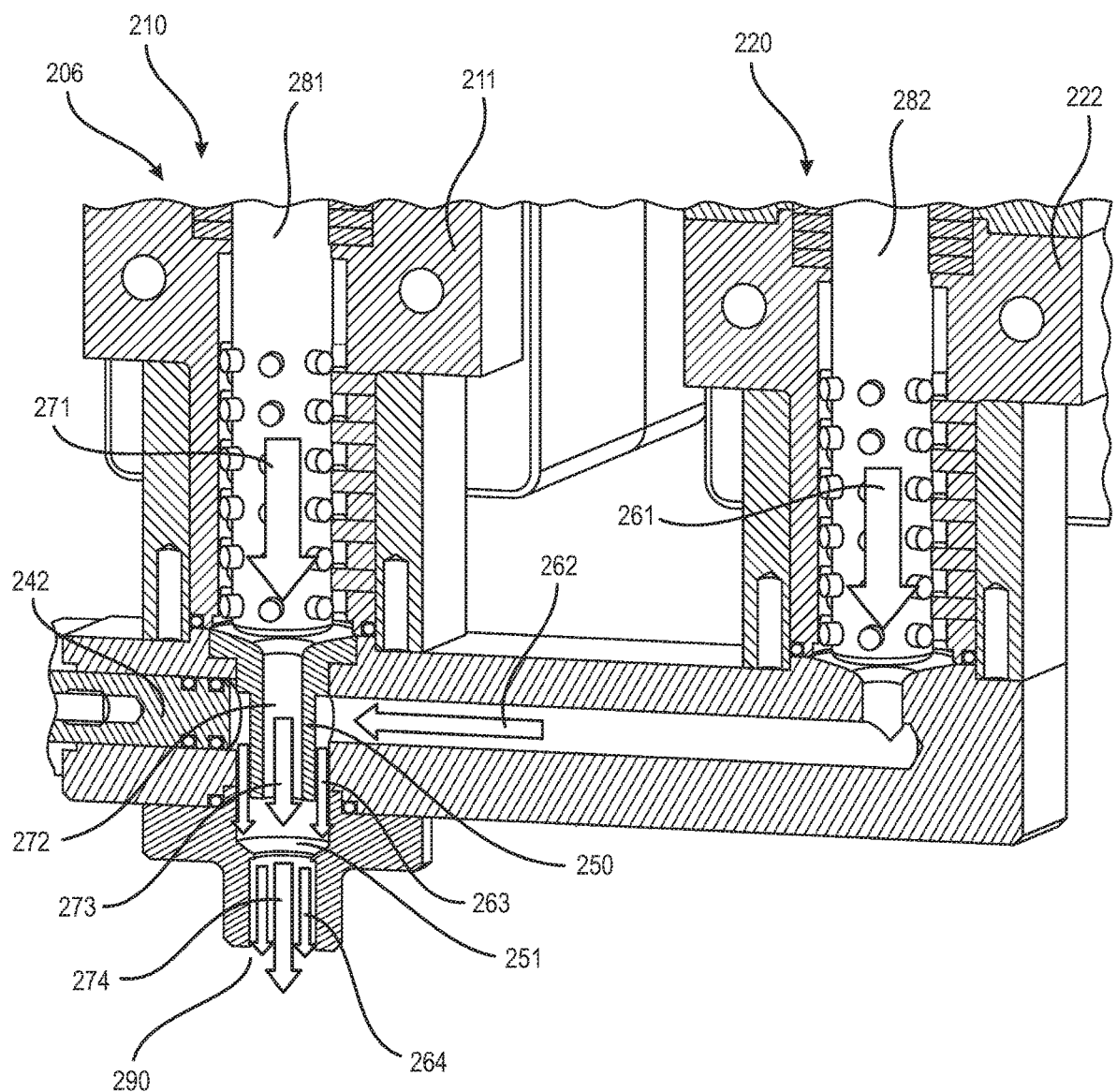
FIG. 8 is a cutaway perspective view of a coextrusion deposition apparatus comprising parallel dynamic mixing apparatuses according to an embodiment of an additive manufacturing system according to the disclosure.

In an alternative embodiment of the additive manufacturing system 100 shown in FIG. 8, a deposition apparatus 206 is arranged for coextrusion of material blends having different and discrete properties. Multiple dynamic mixing modules, receiving material having different properties, are arranged in parallel. For instance, a first dynamic mixing module 210 may comprise an impeller 281 housed within a block 211, blending and actuating a first material in a flow direction 271 towards a nozzle 290.

A second dynamic mixing module 220 comprises a second impeller 282 housed with a second block 222 and blends and actuates a second material in a flow direction 261 towards the nozzle 290. As in the deposition apparatus 106 described previously, the impellers 281, 282 blend elastomeric materials, including, for example, two-part silicone materials and may provide a dynamic mixing of the two material parts to create a smooth, consistent material blend. Each dynamic mixing module 210, 220 may combine and blend first and second parts A, B of separate silicone materials.

The blended materials from the impellers 281, 282 are directed in second respective flow directions 272, 262 towards a coextrusion flange 250. The coextrusion flange 250 is arranged to have multiple layers with a concentric or coaxial relationship, but in other embodiments may have any suitable configuration of layers and shapes. As the blended materials are conducted through the coextrusion flange 250, the coextrusion flange 250 directs the blended materials in a third respective flow direction 273, 263.

The coextrusion flange 250 may comprise a flange defining a central aperture and an outer aperture, the outer aperture concentric with the central aperture and separated by a flange wall. The material from the second dynamic mixing module 220 may be directed through the outer aperture as the material from the first dynamic mixing module 210 is directed through the inner aperture, for example.

At a distal or nozzle-facing end of the coextrusion flange 250, the first and second blended materials having different properties are conducted into a combination chamber 251, in which the blended materials are no longer separated by the flange wall but rather are combined in a concentric and laminar relationship. Because the first and second blended materials are pre-blended when they are arranged in and pass through the combination chamber 251, no blending of the two blended materials is necessary, but rather the blended materials—one forming an outer layer and one forming an inner concentric layer, for example—may abut each other and consequently chemically bond to each other after curing, while retaining distinct material properties.

In an embodiment, the first blended material forming the inner layer may be a low-temperature-curing elastomeric material, arranged to cure and solidify rapidly upon deposition. By contrast, the outer layer may be a high-temperature-curing elastomeric material, arranged to cure more slowly upon deposition, so the outer layer may form chemical bonds due to its uncured state with adjacent and subsequently deposited features. This arrangement allows for a bulk of a deposited material, which may be a continuous filament, to be quickly cured such that smearing is minimized, but allowing for sufficient bonding between adjacent filaments to occur for the mechanical strength of the formed article.

After the blended materials have been combined but not blended in the combination chamber 251, the combined material is conveyed along respective coaxial flow paths 274, 264 towards the nozzle 290, where the combined material, owing to the smooth consistency afforded by the dynamic mixing at the impellers 281, 282, may be deposited as continuous filaments, discrete points or dots, or as continuous films or layers in an additively manufactured article.

As the additively manufactured article is formed layer by layer, filament by filament, drop by drop, or by combinations of different deposition patterns, the properties of the materials may be dynamically changed, such that a first region of the article may comprise a certain durometer, elasticity, mechanical strength, color, curing rate, and/or other property, while subsequently deposited regions may comprise different durometers, elasticities, mechanical strengths, colors, curing rates, and/or other properties, while being continuously additively manufactured. This arrangement is made possible by the dynamic mixing capabilities of the deposition apparatus 206 and the precision blending of particular materials afforded by the first and secondary dispensing systems and displacement pump as described above, which conducts the materials to the deposition apparatus 206 without necessarily blending the different materials.

For details on the structure provided by the system, method, and components thereof, reference is made to the aforementioned co-pending application Ser. No. 16/680,959, which describes discretely and continuously deposited filaments of elastomeric material. The deposited material is described in the preferred embodiment of a plurality of filaments that may abut and are adjacent in x-, y- and z-coordinates/planes to form a definitive article. The filaments are deposited in an uncured or at least partially cured state while retaining the deposited shape. The nozzle and thus the filaments may be adapted for minute filaments or deposited material, such as a 0.1 mm diameter, or other shapes and sizes. In embodiments, nozzles of different shapes and diameters may be provided having any number of different arrangements of shapes, sizes, and concentric or axially arranged layers of material.

While the depicted embodiment describes a system wherein two parallel systems merge to form a combined material having discrete layers with different properties, it will be appreciated that any number of parallel systems may be provided to form combinations of materials having any number of properties. For example, a combined material may be formed from two parallel systems and arranged to have a laminar arrangement, with two sheets of combined but unblended materials, which may be further arranged with and attached to filaments having discrete inner and outer layers formed in another pair of parallel systems.

The parallel systems may be arranged, in certain embodiments, to provide blended material to the coextrusion flange 250 or the combination chamber 251 dynamically. In embodiments, a first parallel system may deliver a first blended material as an inner layer of a continuous filament and a second parallel system may deliver a second blended material as an outer layer of the continuous filament as described above, while a third parallel system may deliver a third blended material to the second blended material in the outer layer according to a dynamic pattern. For example, at times the third blended material may be added and can be mixed to the desired degree with the second blended material as suitable for a resulting property at a particular location on the additively manufactured article, and at other or subsequent times the flow of the third blended material may be decreased, increased, or discontinued relative to the first and second parallel systems. Any suitable pattern and arrangement of any number of parallel systems, which may be varied by time, by composition, and by how they are arranged relative to each other, is envisioned by embodiments of the disclosure.

In other embodiments, multiple systems may be operated in parallel and/or in series. For instance, in the example depicted above, the first parallel system may blend materials that are themselves a blend of multiple materials and blended according to the embodiments of the disclosure. That is, the first parallel system may blend one or more streams of material that are each blended in a deposition head or dynamic mixing module according to the embodiments. There is no intention to limit the possible configurations of different shapes, properties, and arrangements.

In certain embodiments, the deposition apparatus 206 may produce filaments, points, or layers that are hollow or comprise apertures or other textures. In place of the inner layer of material provided by the impeller 281, a single outer layer of material may be provided around a flange to produce a hollow interior that reduces the weight and bulk of an additive manufactured article. Gaps, apertures, or other textures may likewise be provided as suitable to vary any number of properties of the deposited material or filament.

Figure 9:
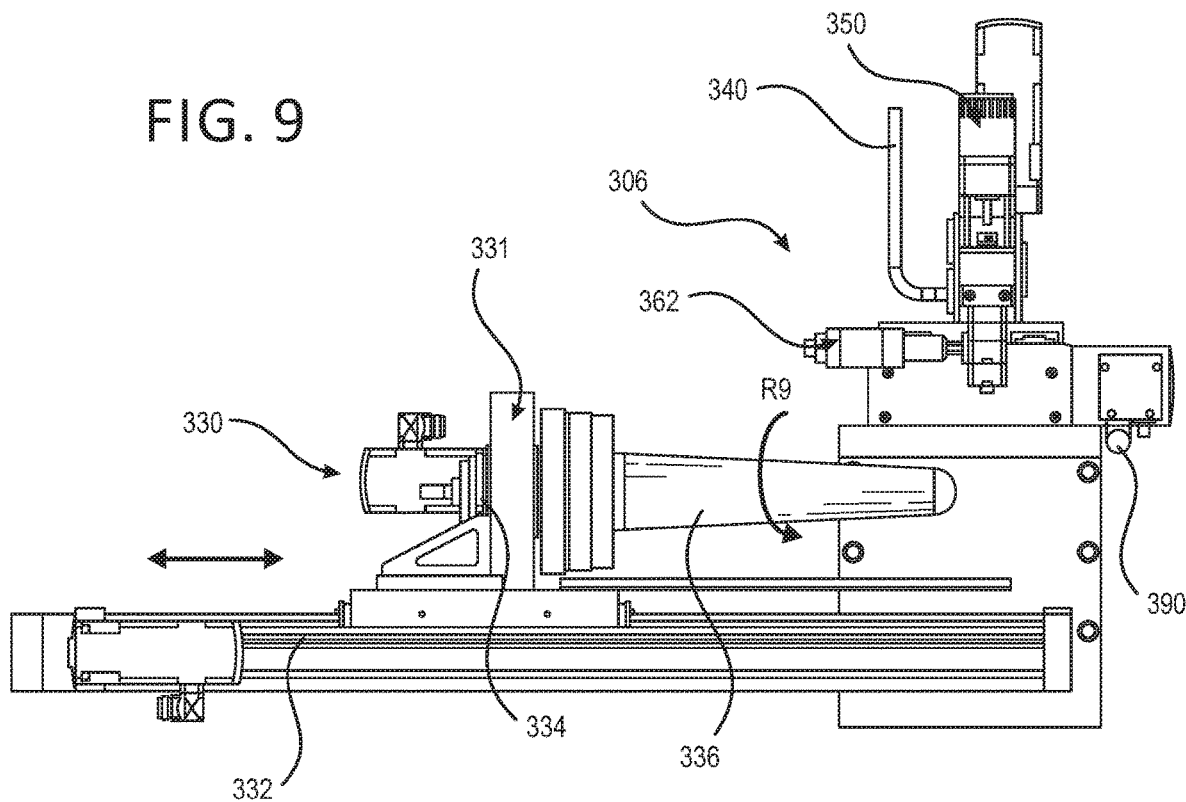
FIG. 9 is an elevational view of a deposition apparatus and a deposition substrate according to an embodiment of an additive manufacturing system according to the disclosure.
Figure 10:
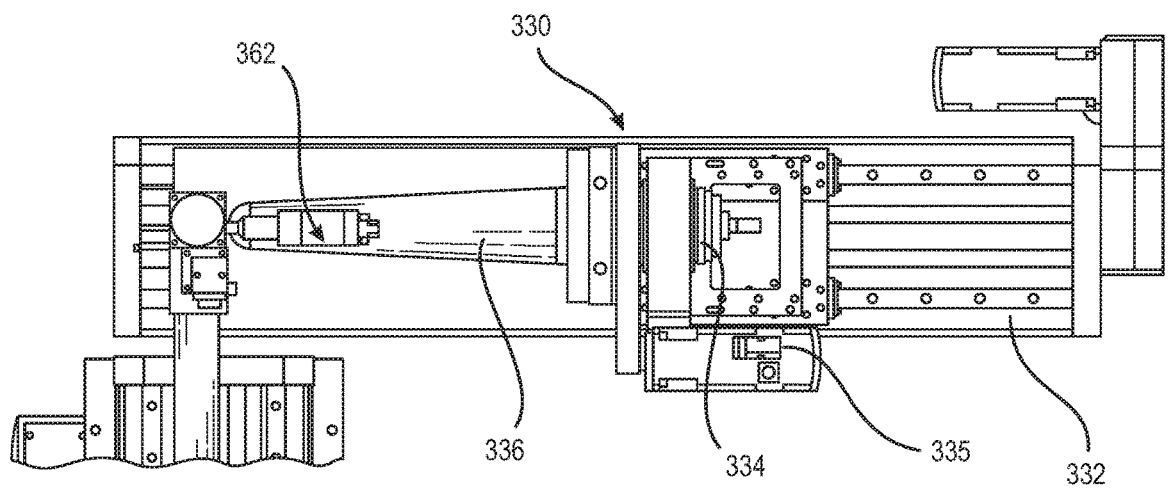
FIG. 10 is a plan view of the deposition apparatus and deposition substrate of FIG. 9.

In another embodiment of an additive manufacturing system and components thereof shown in FIG. 9, a deposition apparatus 306 may receive materials according to the previously described embodiments from first and secondary dispensing mechanisms and/or displacement pumps. The deposition apparatus 306 is also equipped with a dynamic mixing module 350 and a pneumatic stop valve 362 to allow for precise depositions of material from nozzle 390, as described previously. While the nozzle 390 is shown as being arranged downwardly of the dynamic mixing module 350 and pneumatic stop valve 362, it will be appreciated that the components of the deposition apparatus 306 may take any suitable configuration, shape, or order, as described in greater detail below.

In addition to the deposition apparatus 306, a deposition substrate 330 is provided to enable dynamic depositions of material. The deposition substrate 330 may provide a movable substrate on which to deposit an article. This arrangement allows for multiple orders, layers, and directions of additive construction, increasing the flexibility of the additive manufacturing process. The deposition substrate 330 may comprise in the depicted embodiment a rotating mandrel 336, which is configured to rotate in a direction R9 as the deposition apparatus 306 deposits polymeric material on a surface thereof. As the rotating mandrel 336 rotates in the direction R9, not only may the deposition apparatus 306 deposit material in different patterns and orders along the surface of the spinning rotating 336, but the rotating mandrel 336 may also advantageously overcome the deleterious effects of gravity on the additive manufacturing process.

It has been surprisingly found that as the rotating mandrel 336 rotates in the direction R9, the counteraction of centripetal and centrifugal forces acting on the deposited material on the surface of the rotating mandrel 336 prevents unwanted deformation of the article, especially as components thereof grow in height, weight, or other dimensions and as the material is being fully cured. The centripetal and centrifugal forces, operating oppositely in directions pointing inward toward the center of the rotating mandrel 336 and outwardly of the center of the rotating mandrel 336, operate to prevent the growing article, formed from deposited material, from drooping laterally, collapsing, or otherwise changing its configuration as happens to ubiquitously in existing 3D-printing systems that utilize a rotating build surface. While the rotating mandrel 336 is shown as having a conical configuration, any other shape or configuration may be utilized.

By providing the rotating mandrel 336 in combination with the deposition head 306, the problems of existing 3D-printing systems, including those that utilize rotating surfaces, requiring the use of cutters, shavers, and drip pans to catch falling material are avoided. Instead, the additive manufacturing system of the disclosure can continuously deposit elastomeric material in filaments, beads, or layers without the known issues of drooping, deforming, or smearing.

A moving rack 332 is provided on which the rotating mandrel 336 is mounted via an attachment block 331. An actuator 334, such as a motor or other suitable device, provides the rotation R9 of the rotating mandrel 336. The rotating mandrel 336 may thus advantageously translate along with the moving rack 332 by means of an actuator 335 to further facilitate patterns and/or layers of deposited through the nozzle 390. In contrast to existing additive manufacturing devices limited to printing only in cartesian coordinates, such as with an ink-jet printer, the additive manufacturing system of embodiments of the disclosure can print in angular coordinates and in any order or pattern necessary. For example, the article deposited and formed on the rotating mandrel 336 may be formed inside-out, with the article being reversed upon removal from the rotating mandrel 336. The article may also be formed right-side-out, with multiple layers being deposited in a woven fashion.

While in the depicted embodiment the rotating mandrel 336 is moved and translated relative to the nozzle 390 by means of the moving rack 332 and the actuator 335, in embodiments the deposition apparatus 306 may be configured to move and translate relative to the mandrel 336. Both the deposition apparatus 306 and the mandrel 336 may move relative to each other as suitable for a particular application. As described above, the ability to move one of the substrate or rotating mandrel 336 and the deposition apparatus 306 relative to each other allows the nozzle 390 to travel along the surface of the rotating mandrel 336 while depositing a continuous filament, bead, or layer of elastomeric material, facilitating an efficient, precise, and continuous build process.

The rotating mandrel 336 may accelerate the curing process of the deposited material by providing a heat-transfer module 335, wherein heat or refrigeration may be provided. For example, the heat-transfer module 335 may comprise tubing that extends along an inner surface of the rotating mandrel 336 to provide heat to the deposited material for accelerated curing. Alternatively, the heat-transfer module 335 may be configured to provide cooling or refrigeration to the surface of the rotating mandrel 336, delaying the curing process as additional layers or filaments of material are deposited, thus facilitating improved bonding between distinct filaments, for example, as subsequently deposited filaments have more time to chemically bond with a previously deposited and as-yet uncured filament. In other embodiments, the heat transfer module may apply heating or cooling to a conductive surface of the rotating mandrel 336.

The heat-transfer module 335 may provide a dynamic heat-transfer profile over a surface of the rotating mandrel 336. Increased heat transfer may be effected at discrete regions of the rotating mandrel 336. For example, the heat-transfer module 335 may utilize a heated fluid provided by a pump or other actuator (now shown) to a channel near a surface of the rotating mandrel 336 as indicated by the controller to increase a rate of curing of recently deposited material, while another surface of the mandrel 336 is provided with a lower flow rate of the heated fluid; this may help ensure that the material deposited there can bond to other subsequently deposited filaments.

In a variation, the deposition apparatus 306 may move in relation to the deposition substrate 330, where both the deposition apparatus 306 and the deposition substrate 330 may move in relation to the other, or both may move. The deposition substrate 330 may translate as a rotating mandrel 336 and translate in a direction, such as along a horizontal direction or plane in the depicted embodiments, according to the desired article. In each instance, the deposition apparatus 306 is metered (and moved, if so arranged), and the deposition substrate 330 is movable according to the CAM system controlling the manufacturing process.

The CAM system may be any suitable system for directing the operation of the first and second dispensing systems, the deposition apparatus, and the deposition substrate according to embodiments of the disclosure. A computer numerical control (CNC) system may also be utilized in embodiments. A controller or control system can be arranged to receive signals from a plurality of sensors arranged throughout the additive manufacturing system. For instance, sensors may be arranged to detect flow rates of material, pressures, temperatures, positions, velocities, and orientations of particular components.

In embodiments, a sensor can detect the orientation of the deposition substrate relative to the nozzle of the deposition head. A sensor can detect an amount of material in one or more of the vats or reservoirs in the first or primary dispensing system and/or an amount of material accumulated in the proportioning columns of the secondary dispensing system. At least one processor can be configured to direct the operation of the components of the additive manufacturing system, such as the control valves 110A-D, 114A-D, the displacement pump 124, the dynamic mixing module, or the movement of the deposition substrate in rotation and translation, for example. The control system may utilize servo control of various actuators that control the control valves, pumps, deposition apparatus, impellers, pneumatic suck-back valves, and other moving components of the additive manufacturing system to attain an additively manufactured article with regions having different properties at desired locations. The servo control of the components may impart to the system greater accuracy and angular repeatability over other modalities, though the disclosure is not limited to servo control.

Each actuator of the additive manufacturing system that is servo-controlled can be individually and manually tuned to optimize the operation of the system during the additive manufacturing of a particular article. The operation of the servo-controlled actuators that control the dispensing systems, the deposition apparatus, and the deposition substrate can be optimized and adjusted during use based on a process control scheme using a control loop. For example, PID (proportional-integral-derivative) control in any suitable variety such as parallel, series, or expanded form, PI (proportional-integral) control, PD (proportional-derivative) control, proportional control, two-position control, feedback, feedforward, or model-predictive control, combinations thereof, and/or any other suitable process control scheme may be used to control the additive manufacturing system.

The controller may further comprise any suitable utility for converting CAD files or other files into instructions for the additive manufacturing system. The utility for converting CAD files or other files into suitable instructions may account for different properties necessary or desired at different locations along or throughout an additively manufactured article, such as different colors, elasticities, durometers, etc. Based on the different properties desired, the controller may determine an appropriate blend of materials needed to achieve the desired properties and, based on a desired path that the deposition apparatus may trace across a surface of the deposition substrate, an appropriate time for the determined blend of materials to be fed forward the deposition apparatus, so the determined blend arrives at the nozzle at the desired time and location.

Figure 11:
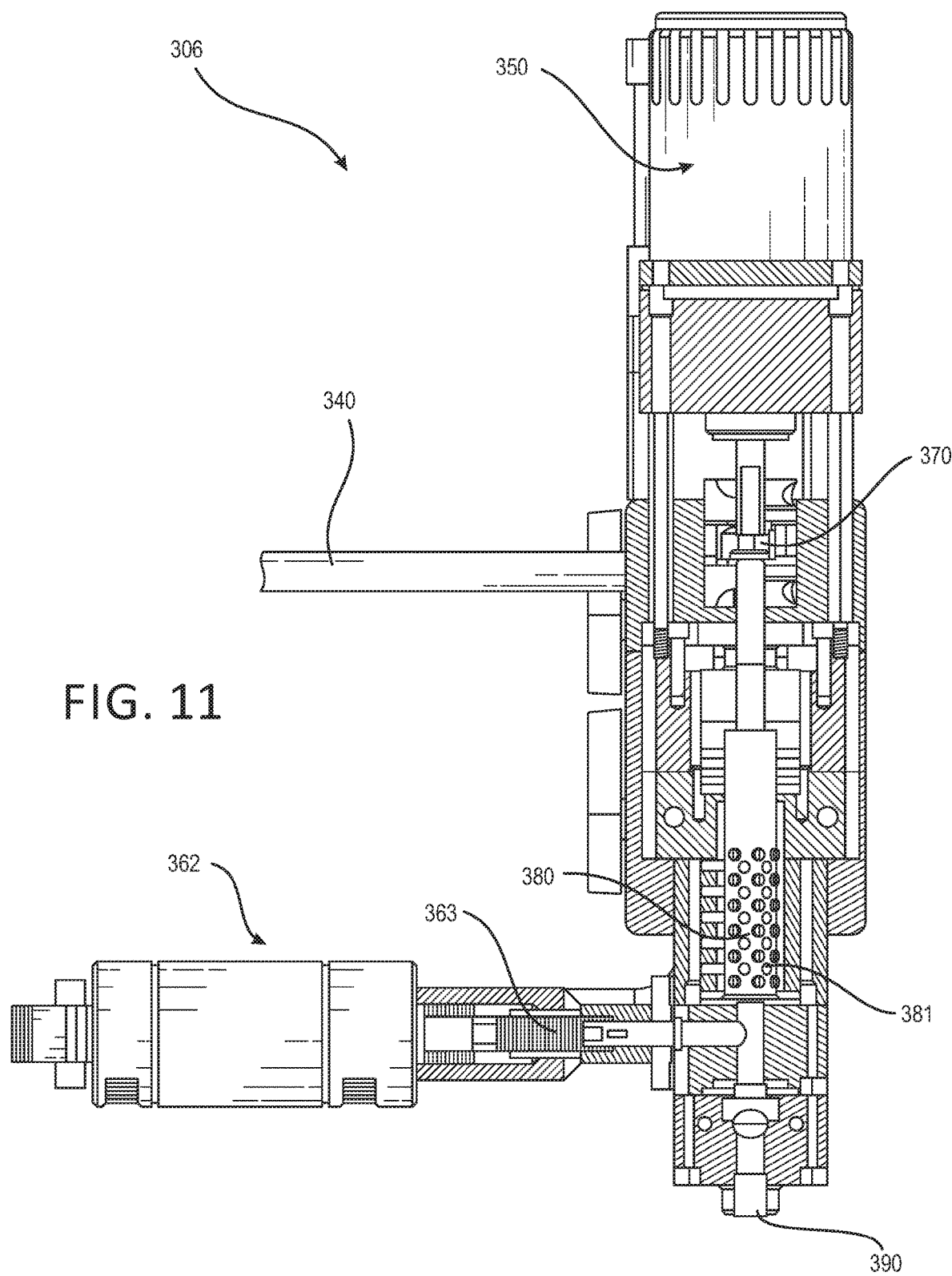
FIG. 11 is an elevational cutaway view of a deposition apparatus according to an embodiment of an additive manufacturing system according to the disclosure.

The deposition apparatus 306 is shown in a cutaway elevational view in greater detail in FIG. 11. As in previous embodiments, the dynamic mixing module 350 may comprise an impeller 380, comprising on an outer surface with protrusions arranged to blend two or more streams of material into a smooth, consistent blended material stream and to drive the material toward the nozzle 390. A material control valve 370 may advantageously control the volume or flow rate of materials into the dynamic mixing module 350 and material may be conducted into the dynamic mixing module 350 via a material line 340. A pneumatic suck-back valve 362 may operate similar to previous embodiments wherein a plunger 363 may be withdrawn to create a negative pressure proximate the nozzle 390 to draw blended material back into the deposition apparatus 306. The operation of the pneumatic suck-back valve 362 serves to mitigate smearing and enable discrete deposits and discrete apertures with a continuous layer or filaments.

The rotating mandrel 336 may be customized to a specific or desired configuration for the final additive-manufactured article. For example, foam or other shapeable and/or additive material may be added onto an outer surface of the rotating mandrel 336 to create a substrate having dynamic or customized dimensions on which the material may be deposited. In other embodiments, the rotating mandrel 336 may comprise or support structures to be integrated into the final article and around which the final article may be additive manufactured. For example, a stiffening matrix or a textile sleeve may be added to the rotating mandrel 336 and the article additive manufactured thereon and/or therearound. In embodiments, the structures are added to the rotating mandrel 336 and/or to the additively manufactured article during or after the deposition process.

In embodiments, an article may be additive manufactured on a planar substrate and then mounted on the rotating mandrel 336 for further depositions. In an example, a textile material arranged to form an outer layer of an elastomeric liner may be additively manufactured with certain elastomeric structures such as seal-in bands or other frictional features on a planar surface. The textile material is then mounted onto the rotating mandrel 336, after which a silicone liner may be additively manufactured by the system of the disclosure over the textile material.

Other combinations of pre-processing steps and pre-arranged materials are likewise envisioned. Additionally, the additively manufactured article may be post-processed in further steps; for instance, the additively manufactured article may be removed from the rotating mandrel 336 after the deposition process is complete and further additive manufacturing steps may be performed on a rotating planar surface or a non-rotating build surface.

The configuration of the nozzle 390 may be dynamic and may change by means of an actuator during deposition to build up particular structures or articles. In embodiments, the nozzle 390 may take a horizontal configuration relative to the rotating mandrel 336 near a base of the structure being deposited on the rotating mandrel 336 and may transition to a vertical configuration nearer a top surface of the structure being deposited on the rotating mandrel 336. In embodiments, the deposition apparatus 306 may be arranged to deposit material in a spiral pattern around the rotating mandrel 336, attaining a weaving pattern with desired characteristics in terms of strength and elasticity while minimizing the amount of material used. The actuator may also change a configuration of the nozzle shape, such that as a continuous filament is being deposited, a larger filament or different shape of filament may be deposited at certain regions of the article without breaking continuity of the continuous filament. This allow for different properties to be imparted to the additively manufactured article at desired locations.

Figure 12A:
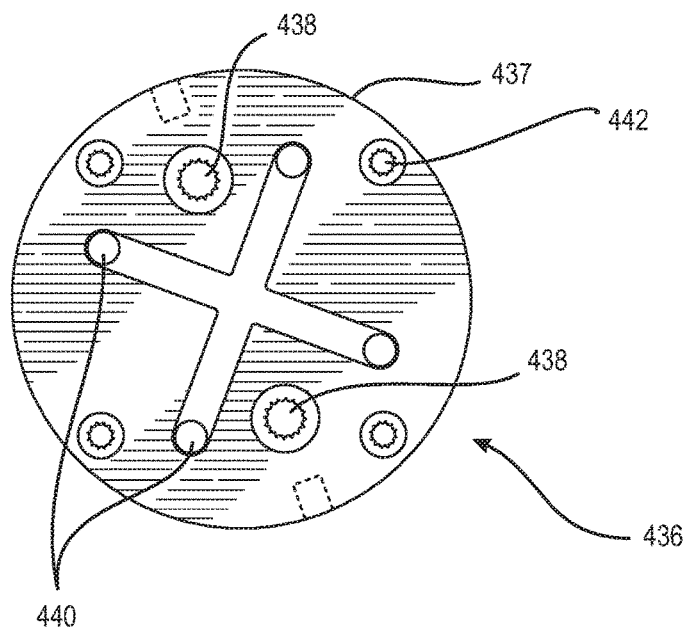
FIG. 12A is a plan view of a deposition substrate according to the additive manufacturing system of FIG. 9.
Figure 12B:
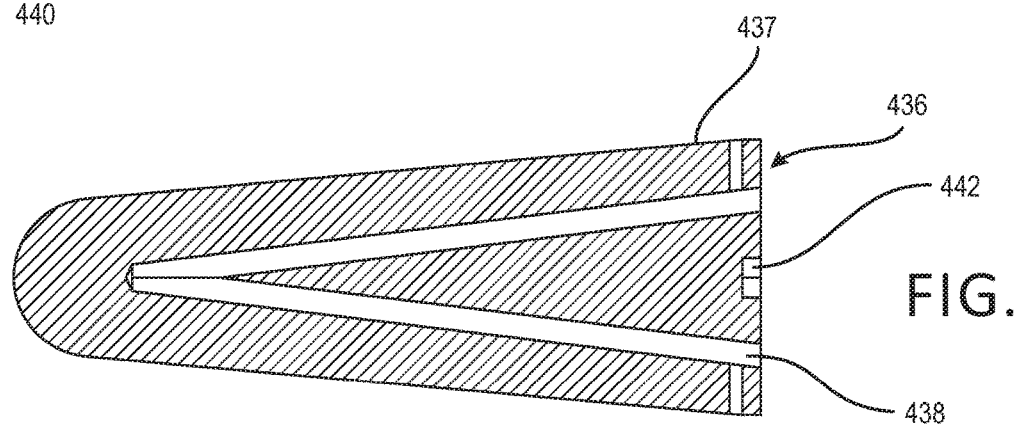
FIG. 12B is a cutaway elevational view of the deposition substrate of FIG. 12A.
Figure 12C:
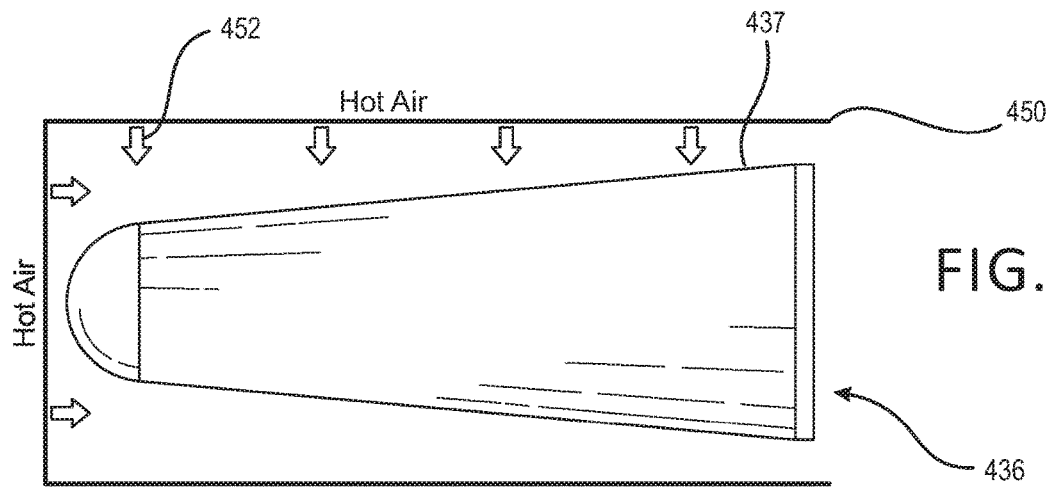
FIG. 12C is an elevational view of the deposition substrate of FIG. 12A according to an embodiment.

As seen from FIGS. 12A-12C, the deposition substrate such as a rotating mandrel 336 may be provided with heat-transfer channels for cooling and for heating. Cooling channels 438 may extend from a backside of the rotating mandrel 436 and through a thickness of the rotating mandrel 336. The cooling channels 438 may define a "v" shape corresponding to a conical shape of the rotating mandrel 436 and may join near a distal or front end of the rotating mandrel 436. As such, one of the cooling channels 438 can define an inlet, and another can define an outlet such that a current of cooling media is provided through the cooling channels 438.

The cooling channels 438 may be connected with an attachment block as described in foregoing embodiments in any suitable manner, and the cooling medium may be any suitable medium, such as cooling water, refrigerant, a gas, or any other suitable medium. The depicted embodiment and description of the cooling channels 438, as with the depiction of the rotating mandrel as being conical in shape, is merely exemplary, and any suitable configuration may be adopted.

For instance, in embodiments in which the substrate is a rotating planer surface, the cooling channels 438 may be defined through the thickness of the planer surface in any suitable configuration. The cooling channels 438 may have a symmetric or asymmetric configuration and may provide heat transfer in an even and consistent manner or may provide heat transfer in a dynamic manner and at desired locations. Also shown is an attachment 442 at which the rotating mandrel 436 can removably attach to the attachment block by any suitable means. The removable attachment of the rotating mandrel 436 can facilitate the use of differently shaped substrates in the additive manufacturing system for improved customizability of the additively manufactured articles and for operational flexibility.

Also shown are heating channels 440. As with the cooling channels 338, the heating channels 440 can be configured to provide heat to a surface of the rotating mandrel 336 in any suitable configuration. In embodiments, the heating channels 440 can be configured to receive cartridge heating modules. The cartridge heating modules may be controlled by the CAM system to ensure that a desired amount of heat yielding a desired surface temperature is provided, this serving in embodiments to expedite a curing process of the deposited material. The heat provided by each of the cartridge heating modules may be dynamic in that a region of the surface of the rotating mandrel 436 may be heated to promote curing while heat is not applied to another region, for instance to delay a curing process until a subsequent filament is deposited. In other embodiments, the heating channels 440 can be configured to receive a heating medium, such as a heated fluid or to use embedded electrical heating elements.

Turning to FIG. 12C, a shield 450 may be provided to surround the rotating mandrel 436. The shield 450 may be arranged with apertures or other means that facilitate currents 452 of heating fluid such as hot air to flow inward and contact a surface 437 of the rotating mandrel 436. The currents 452 within the shield 450 may further expedite the curing process. Alternatively, the currents 452 may have a temperature lower than a temperature of the deposited material to delay the curing process until subsequent filaments, or layers can be deposited.

Figure 13A:
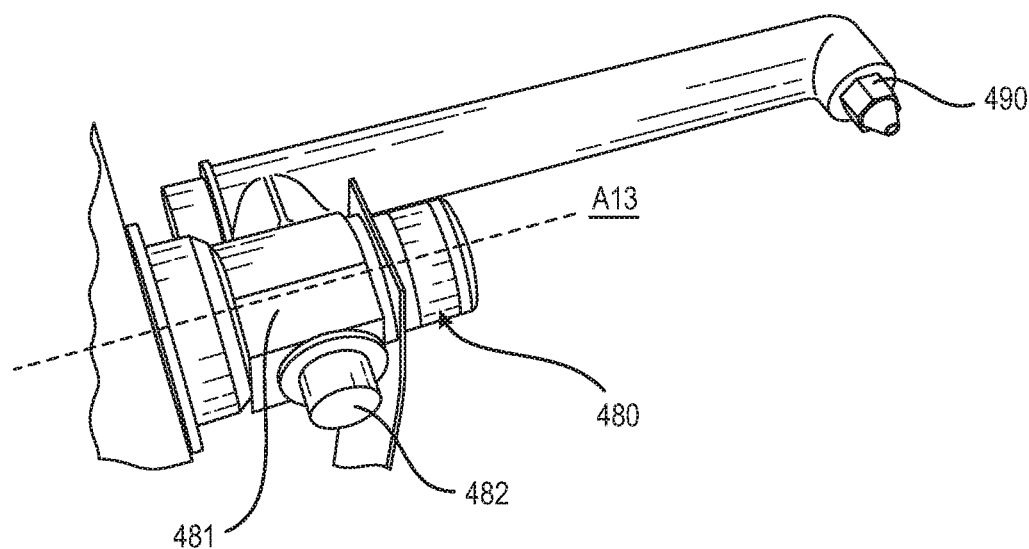
FIG. 13A is a perspective view of a nozzle of a deposition apparatus according to an embodiment.
Figure 13B:
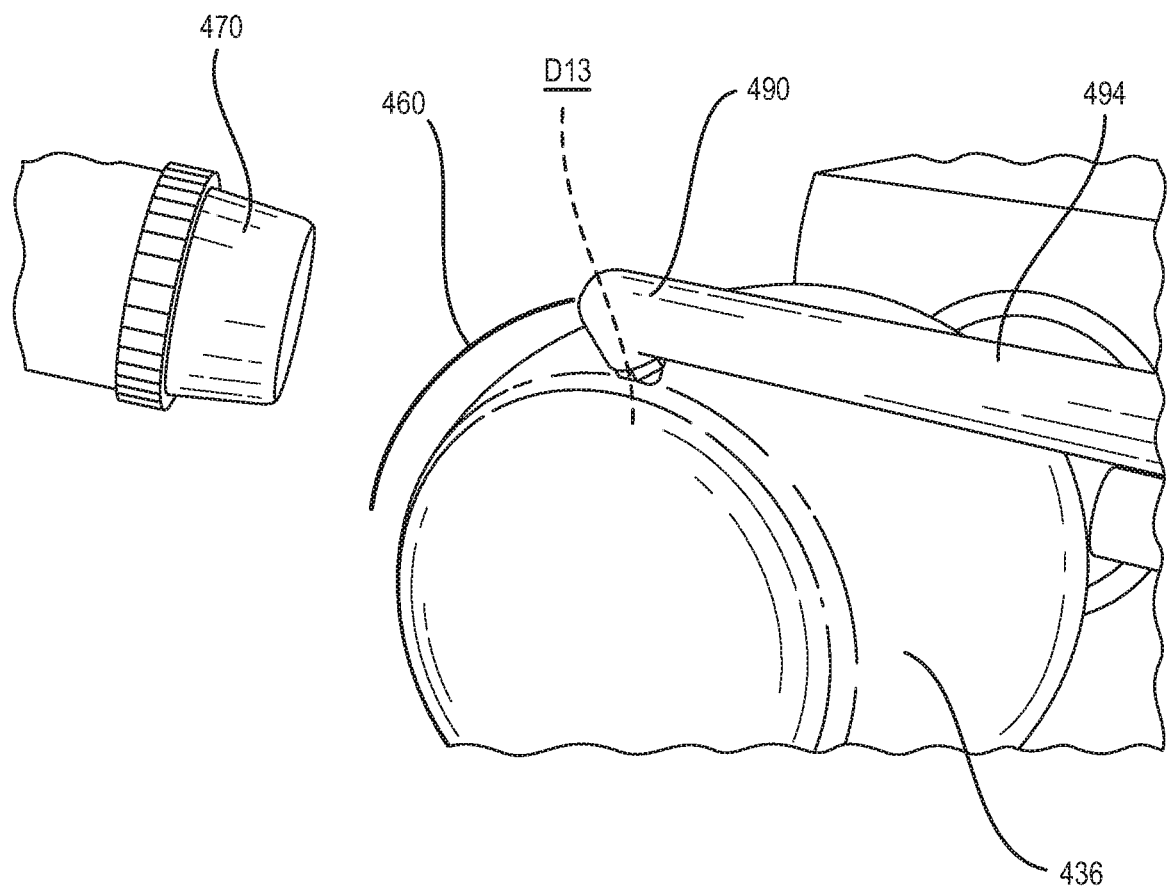
FIG. 13B is a perspective view of the nozzle of FIG. 13A and a deposition substrate according to an embodiment.

FIGS. 13A and 13B show an embodiment of a rotating nozzle 490 according to another embodiment of the disclosure. Because the substrate may define an asymmetrical shape, it can be desirable to provide another axis of rotation at the deposition head according to embodiments of the disclosure to ensure that the nozzle deposits material at an angle that is normal to any given point on the surface of the substrate. In the case of the rotating mandrel 436, the mandrel 436 due to its substantially conical configuration can define a profile or curvature 460. To allow the nozzle 490 to deposit material at an angle D13 that is normal to the profile 460, the nozzle 490 can be a rotating nozzle 490 that extends away from the deposition head on an arm or shaft 494. The nozzle 490 may be rotated about an axis A13 by an actuator 480, which may attach to the deposition head at an attachment 482 comprising a body 481.

To accommodate the profile 460 without disruption, the deposition substrate 436 and/or the deposition apparatus may comprise an actuator (not shown) configured to change a vertical position of the deposition substrate 436 relative to the deposition apparatus. The actuator allows the nozzle 490 to contact the surface of the deposition substrate 436 at a desired distance suitable for depositing the elastomeric material regardless of the profile 460, which may otherwise change a distance by which the deposition substrate 436 and the nozzle may be spaced apart. This may be particularly beneficial in instances when the deposition substrate 436 is asymmetric so as to define an asymmetric final article shape.

The deposition apparatus may be further provided with curing means 470 configured to expedite a curing process further. The curing means 470 may be a UV lamp or a heat lamp. By providing the curing means 470 in combination with the deposition apparatus, deposition substrate, and the material blend as described herein, the additively manufactured product may overcome the problems of existing processes which require cutters, shavers, and drip means to address the problem of deposited material being imprecisely deposited and poorly cured in situ to define an article with precise features having desired properties.

By contrast, the additive manufacturing system of the disclosure, by combining the use of a deposition apparatus provided with blends of materials having tailored properties and a deposition substrate according to the embodiments, enables the deposition and additive manufacturing of articles having tailored properties at desired locations while providing a cleaner and continuous process for additive manufacturing of elastomeric articles.

Figure 14A:
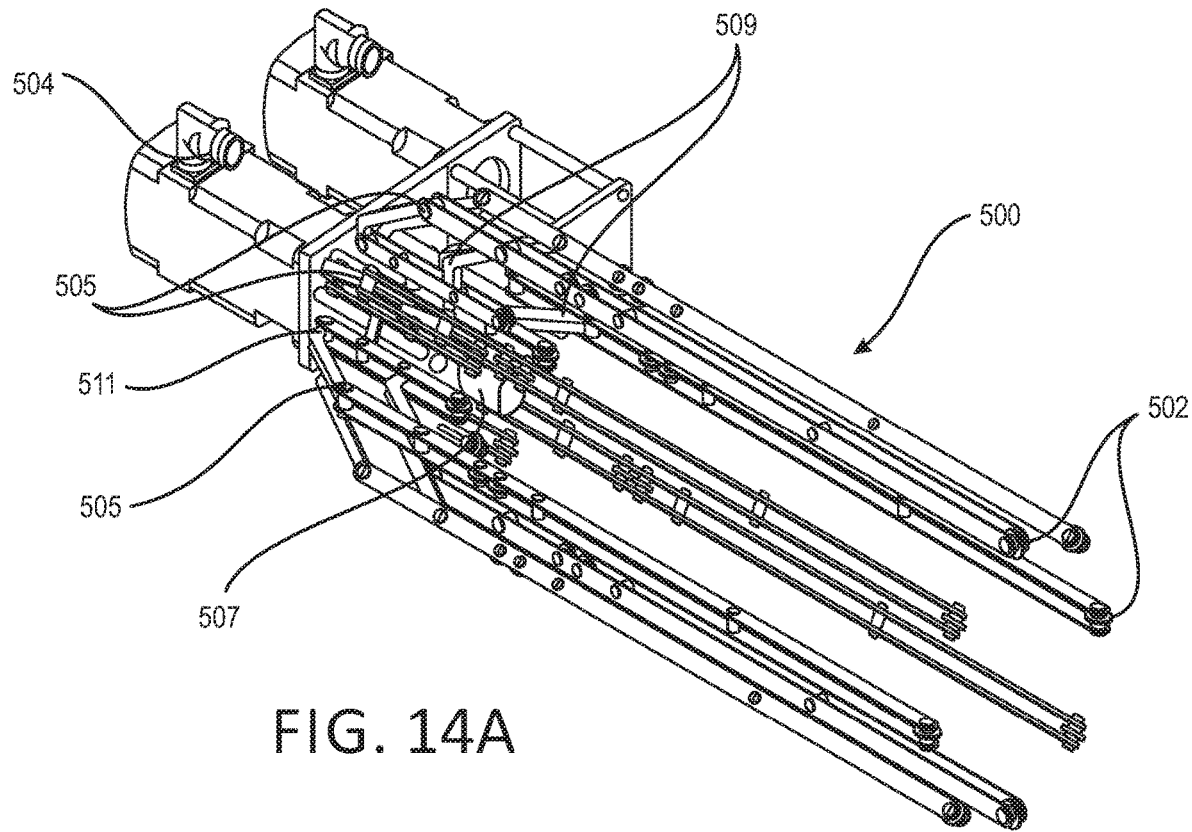
FIGS. 14A and 14B are perspective views of a mounting mechanism according to an embodiment of the disclosure.
Figure 14B:
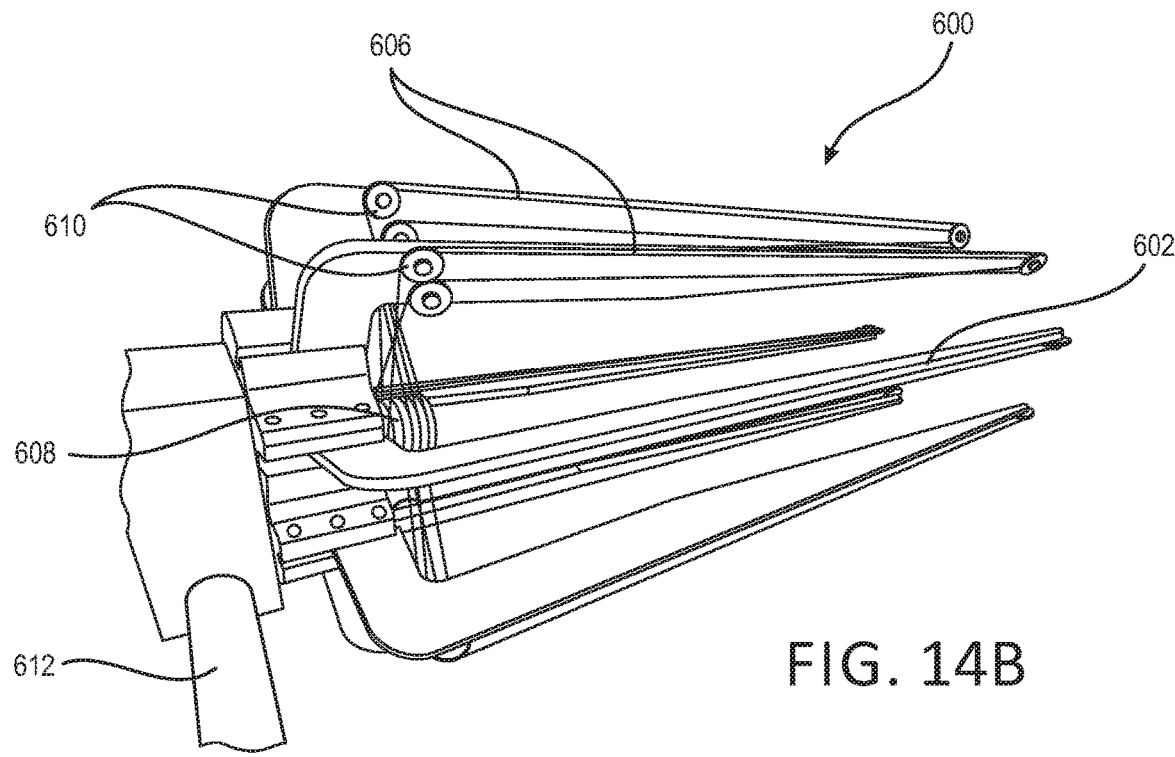

FIGS. 14A-D show embodiments of a mounting mechanism 500, 600 configured to cooperate with the deposition substrate. FIGS. 14A and 14B show a mounting mechanism 500 according to a first embodiment and configured to cooperate with a rotating mandrel according to embodiments disclosed herein. The mounting mechanism 500 may comprise several arms 502 that function as end effectors and are configured to arrange or place a separate article, such as a non-3D-printed article, upon the deposition substrate so as to engage with the additively manufactured article.

The mounting mechanism 500 may be used when assembling devices that utilize pre- or post-processing steps to combine an additively manufactured article and a separate article to form a device. An exemplary device formed using a mounting mechanism according to embodiments is a liner in which a textile sleeve is applied to an additively manufactured silicone structure, but the disclosure is not limited to this embodiment.

The end effectors 502 can be arranged about the mounting mechanism 500 to form an enclosure or circumference substantially about the deposition substrate with which the mounting mechanism 500 is configured to cooperate. The end effectors 502 are adjustable to accommodate differently sized deposition substrates and additively manufactured articles built thereon. The end effectors 502 can be rotated or pivoted about at least a first joint 505 to extend the circumference defined by the end effectors 502, allowing the mounting mechanism 500 to engage with a larger deposition substrate.

The end effectors 502 can be supported relative to a central actuator 507 by arms 509 that extend outwardly from the central actuator 507. The end effectors 502 can further be configured to pivot about a second joint 511 to maintain a substantially parallel relationship between the end effectors 502 and the deposition substrate. The central actuator 507 can be driven by at least one motor driver 504. Alternatively, the end effectors 502 can each be actuated independently of each other to enable the mounting mechanism 500 to engage with an asymmetrically or eccentrically shaped deposition substrate.

In use, a separate article such as a textile sleeve is positioned on end effectors 502 to define a circumference relative to the deposition substrate. The mounting mechanism 500, and the end effectors 502 can be adjusted, so the textile sleeve conforms in size and shape to the deposition substrate. The mounting mechanism 500 can be configured to translate relative to the deposition substrate to position the deposition substrate within a cavity or space defined between the end effectors 502, so the textile sleeve surrounds and engages the deposition substrate.

Figure 14C:
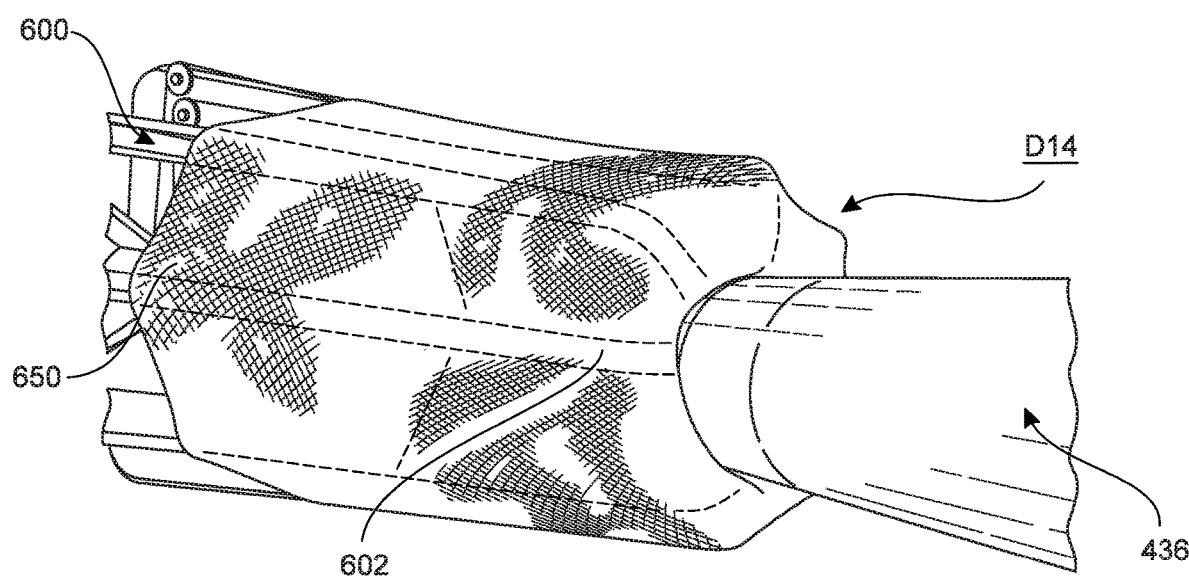
FIG. 14C is a perspective view of a mounting mechanism and a deposition substrate according to an embodiment of the disclosure.

In a second embodiment shown in FIGS. 14C-D, a mounting mechanism 600 likewise comprises end effectors 602 arranged to define a circumference or enclosure around a deposition substrate. The end effectors 602 may support cable actuators 606 that can be routed along a length of the end effectors 602 by routing mechanisms 610, which may be pulleys, guides, or any other suitable routing mechanism. The cable actuators 606 can be jointly actuated by a central actuator or spool 608 or may be provided with respective actuators.

The cable actuators 606 can serve to move a separate article, such as a non-3D-printed article including a textile sleeve, toward a distal end of the end effectors 602 for placing on the deposition substrate. As with the embodiment of FIGS. 14A-B, the mounting mechanism 600 may be actuated relative to the deposition substrate such that the separate article mounted on end effectors 602 can substantially surround the deposition substrate, such that as the cable actuators 606 move the separate article toward the distal ends of the end effectors 602, the separate article can be engaged with and onto the deposition substrate and the article being or recently additively manufactured thereon.

The cable actuators 606 may operate to move the textile sleeve at different speeds at different times to precisely orient the separate article on the deposition substrate in the desired configuration. In an embodiment, the separate article is a textile sleeve to be placed on an elastomeric liner additively manufactured upon the deposition substrate. By arranging the textile sleeve on the elastomeric liner using the mounting mechanism 600, an automated, and therefore more precise, mounting operation is facilitated, as the imprecisions and risks associated with manually mounting the separate article on the deposition substrate are avoided.

While a rotating mandrel having a conical shape has been shown and described, the deposition substrate may have any suitable configuration based on any desired final article to be additively manufactured. The deposition substrate may be substantially planar, cylindrical, rectilinear, or any other suitable shape. The deposition substrate need not be symmetric and can define any suitable profile. The additive manufacturing system according to the disclosure can be utilized to additively manufacture any suitable article, including elastomeric breast implants, liners, medical implants such as tubing and seals, joint component replacements, surgical tools, and any other suitable device.

In embodiments where the additive manufacturing system is configured to produce an elastomeric breast implant, the deposition substrate may be provided with a shape and/or rotation configuration that corresponds to a desired shape of the elastomeric breast implant. Because elastomeric breast implants often comprise an upper portion and a lower portion that can define an outer shell inside of which an elastomeric gel, saline solution, or other suitable material can be contained, the deposition substrate of the additive manufacturing system may be configured to additively manufacture a continuous or substantially continuous outer shell from elastomeric material such that the outer shell has desired properties at desired locations. For example, a lower portion arranged to be implanted inwardly can have a greater rigidity or lower elasticity than an upper portion arranged to be implanted outwardly of the lower portion. The upper portion may be additively manufactured to have, for example, greater elasticity in regions to attain a suitable shape that may be asymmetric.

Because elastomeric breast implants are often asymmetric, the deposition substrate can be arranged to move relative to the deposition apparatus, whether by rotation, translation, or otherwise, to define the asymmetric shape of the elastomeric breast implant. In embodiments, the deposition substrate can be a planar surface on which the lower portion of the outer shell is first deposited by the additive manufacturing system as the planar deposition substrate rotates relative to the deposition apparatus.

The additive manufacturing system can be operated so as to impart desired properties such as durometer, elasticity, and other properties at desired points along the lower portion. The deposition apparatus may deposit continuous filaments that have varying properties along a length of the continuous filament and which may chemically bond with adjacent and/or subsequently deposited filaments to define a continuous elastomeric body with desired properties at desired locations.

An upper portion can be built from and on the lower portion to define a continuous outer shell and may comprise filaments that are continuous with filaments that define the lower portion, while nevertheless having different properties to define the upper portion. The filaments may be interspersed with continuously deposited layers and/or drops of an elastomeric material such that the outer shell may define any suitable texture; for example, in embodiments the outer shell may comprise a textured outer surface comprising ridges and corresponding valleys. In other embodiments, outer surfaces of the outer shell may be substantially smooth. A dynamic texture and properties may be defined through a thickness of the outer shell, with a smooth and rigid inner surface of the outer shell configured to encase the silicone gel or saline inside the implant, and with a textured outer surface configured to disrupt capsular tissue after the implant has been placed. The described embodiment is merely exemplary and is not limiting.

In embodiments, the deposition substrate may be an additively manufactured article with dimensions corresponding to the custom dimensions of an article to be printed thereon. For instance, in embodiments wherein the additive manufacturing system is utilized to create an elastomeric liner for a limb residuum, a user's limb dimensions can be measured and used to additively manufacture or otherwise prepare the deposition substrate to match the user's limb. The additively manufactured elastomeric liner can then correspond closely to the user's limb.

By providing an additive manufacturing system, method, and corresponding components for making elastomeric structures according to the disclosure, the limitations of existing additive manufacturing methods—namely, using low quality polymeric materials to facilitate better deposition, the effects of gravity distorting a manufactured article, or the monolithic structure of the article, with a single material having a single set of properties forming the entire structure—are addressed. The additive manufacturing system provides a dynamic system for selecting from infinitely many combinations of materials and properties to create manufactured articles with dynamic properties at desired regions within the printed article. The deposition apparatus provides for the creation of smooth and consistently blended materials for reliable and consistent properties at desired regions. The system may be arranged for co-extrusion of multiple layers of materials having different properties. A deposition substrate may advantageously provide a dynamic surface on which to build an additive manufactured article.

It is to be understood that not necessarily all objects or advantages may be achieved under an embodiment of the disclosure. Those skilled in the art will recognize that the additive manufacturing system, method, and corresponding components for making elastomeric structures may be embodied or carried out in a manner that achieves or optimizes one advantage or group of advantages as taught herein without necessarily achieving other objects or advantages as may be taught or suggested herein.

The skilled artisan will recognize the interchangeability of various disclosed features. In addition to the variations described herein, other known equivalents for each feature can be mixed and matched by one of skill in this art to construct an additive manufacturing system, method, and corresponding components for making elastomeric structures in accordance with principles of the present disclosure. It will be understood by the skilled artisan that the features described herein may apply to other types of additive manufacturing systems, materials, and articles.

Although this disclosure describes certain exemplary embodiments and examples of an additive manufacturing system, method, and corresponding components for making elastomeric structures, it nevertheless will be understood by those skilled in the art that the present disclosure extends beyond the specifically disclosed embodiments to other alternative embodiments and/or users of the disclosure and obvious modifications and equivalents thereof. It is intended that the scope of the present disclosure should not be limited by the particular disclosed embodiments described above and may be extended to other additive manufacturing systems and methods, and other applications that may employ the features described herein.

The invention claimed is:

1. A system for additive manufacturing, comprising:
a first dispensing system comprising at least one reservoir capable of holding an uncured liquid silicone material;
a second dispensing system comprising at least one proportioning device and at least one control valve, the secondary dispensing system configured to receive the uncured liquid silicone material from the first dispensing system;
a deposition apparatus comprising a nozzle, a dynamic mixer, and a control valve; and
a deposition substrate;
wherein the deposition apparatus is configured to receive the uncured liquid silicone material from the second dispensing system, to process the uncured liquid silicone material, and to deposit the uncured liquid silicone material onto the deposition substrate;
wherein the deposition substrate is a cylindrical or conical mandrel configured to translate relative to the deposition apparatus in a horizontal direction and to rotate in a direction perpendicular to the horizontal direction.

2. The system for additive manufacturing of claim 1, wherein the deposition apparatus comprises a sonic vibration module.

3. The system for additive manufacturing of claim 1, wherein the deposition apparatus further comprises at least one heating and/or cooling element.

4. The system for additive manufacturing of claim 1, wherein the deposition apparatus further comprises at least one pneumatic suck-back valve.

5. The system for additive manufacturing of claim 1, wherein the dynamic mixer comprises an impeller arranged to rotate.

6. The system for additive manufacturing of claim 1, wherein the deposition apparatus comprises a sonic vibration module upstream from the nozzle.

7. The system for additive manufacturing of claim 1, wherein the deposition apparatus comprises at least one temperature sensor and at least one pressure sensor.

8. The system for additive manufacturing of claim 1, wherein the at least one proportioning device, the at least one control valve of the second dispensing system, the dynamic mixer, and the deposition substrate are servo controlled.

9. The system for additive manufacturing of claim 1, wherein the at least one proportioning device comprises a plurality of proportioning devices and the at least one control valve comprises a plurality of control valves, and wherein the first dispensing system further comprises at least one proportioning device and at least one control valve.

10. The system for additive manufacturing of claim 1, wherein the second dispensing system further comprises a displacement unit configured to receive and transfer the uncured liquid silicone material to the deposition apparatus.

11. The system for additive manufacturing of claim 1, wherein the nozzle is a hollow nozzle configured to deposit the uncured liquid silicone material.

12. The system for additive manufacturing of claim 1, wherein the deposition substrate comprises heating and/or cooling elements.

13. A system for additive manufacturing, comprising:
a first dispensing system comprising at least one reservoir capable of holding an uncured liquid silicone material;
a second dispensing system comprising at least one proportioning device and at least one control valve, the secondary dispensing system configured to receive uncured liquid silicone material from the first dispensing system;
a deposition apparatus comprising a nozzle, a dynamic mixer, and a control valve; and
a deposition substrate comprising heating and/or cooling elements, wherein the deposition substrate is a cylindrical or conical mandrel configured to translate relative to the deposition apparatus in a horizontal direction and to rotate in a direction perpendicular to the horizontal direction;
wherein the deposition apparatus is configured to receive the uncured liquid silicone material from the second dispensing system, to process the uncured liquid silicone material, and to deposit the uncured liquid silicone material onto the deposition substrate; and
a controller configured to operate the first and second dispensing systems, the deposition apparatus, and the deposition substrate using servo control.

14. The system for additive manufacturing of claim 13, wherein the deposition apparatus comprises a sonic vibration module.

* * * * *